US012766302B2

(12) United States Patent
Nalawade et al.

(10) Patent No.: US 12,766,302 B2
(45) Date of Patent: Oct. 20, 2026

(54) DEVICE FOR DISINFECTING AND FLUSHING AN INTRAVENOUS CONNECTOR

(71) Applicant: Becton, Dickinson and Company, Franklin Lakes, NJ (US)

(72) Inventors: Praveen Nalawade, Belgaum (IN); Shishir Prasad, Ramsey, NJ (US); Joyce L. Young-Stewart, Sparks, NV (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 652 days.

(21) Appl. No.: 18/215,372

(22) Filed: Jun. 28, 2023

(65) Prior Publication Data

US 2025/0001156 A1 Jan. 2, 2025

(51) Int. Cl.

*A61M 39/16* (2006.01)
*A61L 2/18* (2006.01)
*A61L 2/26* (2006.01)
*A61L 103/15* (2026.01)

(52) U.S. Cl.

CPC ............. *A61M 39/162* (2013.01); *A61L 2/18* (2013.01); *A61L 2/26* (2013.01); *A61L 2103/15* (2026.01); *A61L 2202/121* (2013.01); *A61L 2202/123* (2013.01); *A61L 2202/17* (2013.01)

(58) Field of Classification Search

None

See application file for complete search history.

(56) References Cited

U.S. PATENT DOCUMENTS 4,334,551 A * 6/1982 Pfister .................. A61M 39/26 604/905
4,610,469 A 9/1986 Wolff-Mooij
6,142,446 A * 11/2000 Leinsing ............... A61J 1/2096 604/905
9,399,098 B2 * 7/2016 Woehr ................ A61M 5/3134
10,391,295 B2 * 8/2019 Ryan ................... A61M 39/162
2005/0151105 A1 * 7/2005 Ryan ..................... A61M 39/26 251/149.6
2008/0264450 A1 10/2008 Baldwin et al.
2011/0054440 A1 3/2011 Lewis (Continued)

OTHER PUBLICATIONS

"PCT International Search Report and Written Opinion in PCT/US2024/035346 dated Oct. 10, 2024, 14 pages".

*Primary Examiner* — Manuel A Mendez
(74) *Attorney, Agent, or Firm* — Servilla Whitney LLC

(57) ABSTRACT

A disinfection and flushing device for an intravenous patient connector requires only a single coupling of a disinfection cap of the device to the patient connector, both to scrub the patient connector and to administer flushing solution through the connector via a flush syringe that is already coupled to a housing portion of the device. The disinfection cap and housing portions of the device are coupled together during the initial patient connector scrub and flush operation. Thereafter, in some embodiments, the housing and its attached, spent flush syringe, are selectively separable from the disinfection cap portion of the device, so that the disinfection cap remains in place on the patient connector. In other embodiments, the entire device, including its cap, housing and the flush syringe that is coupled to the housing, are removed from the patient connector.

26 Claims, 19 Drawing Sheets

(56) References Cited

U.S. PATENT DOCUMENTS

| | | | | |
|---|---|---|---|---|
| 2016/0129235 | A1 * | 5/2016 | Ryan | A61M 39/1011 604/535 |
| 2024/0173535 | A1 | 5/2024 | Prasad et al. | |

* cited by examiner

DEVICE FOR DISINFECTING AND FLUSHING AN INTRAVENOUS CONNECTOR

TECHNICAL FIELD

The present disclosure generally relates to devices for disinfecting and flushing patient connectors used for intravenous (IV) administration of medication and other fluids to or from patients. More specifically, the present disclosure relates to a disinfection and flushing device that requires only one coupling to the patient connector.

BACKGROUND

Vascular access devices (VAD's) are commonly used therapeutic devices and include intravenous (IV) catheters. There are two general classifications of VAD's, peripheral catheters and central venous catheters. Several types of access hubs, ports or valves are coupled to a VAD when delivering a fluid or pharmaceutical. A Luer connector is a common way to couple or join syringes, catheters, hubbed needles, IV tubes, etc. to each other. When VADs are used for medical patient care, there are potential risks of occlusions and contamination of components.

If not properly maintained, VADs can become occluded. To ensure VADs are used properly and do not become occluded, standards of practice have been developed. These standards include a cleaning procedure, which is commonly referred to as a flush procedure or flushing a catheter. VAD standards of practice usually recommend flush procedures be performed after catheter placement, before fluid infusion, and before and after drug administration, blood sampling, transfusions, and parenteral nutrition. The goal of these flush procedures is to confirm catheter patency, avoid drug incompatibilities, ensure the complete drug dose administration, prevent thrombus formation, and minimize the risk of blood stream infections. Flush procedures require diverse types and amounts of flush solutions. Commonly used flush solutions are saline and/or heparin lock solution. The type of flush solution and amount vary depending on the specific type of catheter. After flushing, the practitioner is then able to administer a dosage of medical fluid, followed by a post-administration flushing. Medication delivery and companion flushing through VAD delivery systems also inherently expose the delivery system to potential contamination.

Bacteria and other microorganisms may gain entry into a patient's vascular system from diverse types of patient connectors, including by way of non-limiting example, access hubs, ports or valves, upon their connection to the VAD when delivering a fluid or pharmaceutical. Each patient connector, whether an access hub, port, valve or other type of connection, is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and caps are also incorporated into the Infusion Nurses Standards (INS) guidelines.

In developed markets, when utilizing an IV catheter, a needleless patient connector will typically be used to close off the system and then subsequently be accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." Currently many nursing units mandate the practice of scrubbing the patient's IV connector hub, even if the connector is presently coupled to an existing disinfection cap.

Typically, four disinfection caps and four scrubbing procedures are required to administer a single drug through a VAD system in a Saline-Administration of drug-Saline (SAS) workflow process. The first disinfection scrub prepares the patient's VAD connector for drug delivery and receipt of a first flushing syringe to dissolve potential occlusions within the VAD delivery system and its IV catheter. The first flushing syringe is removed after completion of the pre-flush. Thereafter a second disinfection scrub prepares the catheter hub for connection to a medication delivery syringe. A third disinfection scrub prepares the catheter hub for connection of a second flushing syringe to complete a post-medication delivery flush. Lastly, after removal of the second flushing syringe, a fourth disinfection scrub is performed, followed by sealing of the catheter hub with a cap or a locking syringe. In the case of a or Saline-Administration of drug-Saline-Heparin (SASH) workflow process, a third, heparin flushing procedure is required after the second saline flush, which requires a third flush syringe and a fifth disinfection scrub. When more than one drug is administered to a patient, during the workflow process, each additional drug dose is followed by hub disinfection before initiating the next dispensing task.

Throughout the sequence of procedures necessary to prevent occlusions within VAD systems and to administer medication to a patient there are contamination and microorganism transmission risks that can cause a CRBSI every time a syringe is connected or disconnected from the patient's VAD connector. It would be desirable to minimize the number of VAD connections and disconnections needed to administer one or more drugs to a patient, as well as the number of VAD scrubbing procedures necessary to administer medication to a patient through a VAD hub or other device, in order to reduce contamination risk. Reducing the number of VAD connections and disconnections beneficially would reduce clinician time and reduce the number of syringes and disinfection caps needed to administer one or more medications to a patient.

SUMMARY

The disinfection and flushing device of the present disclosure requires only a single coupling of a disinfection cap of the device to the IV patient connector, both to scrub the patient connector and to administer flushing solution through the connector via a flush syringe that is already coupled to a housing portion of the device. The disinfection cap and housing portions of the device are coupled together during the initial patient connector scrub and flush operation. Thereafter, in some embodiments, the housing and its attached, spent flush syringe, are selectively separable from the disinfection cap portion of the device, so that the disinfection cap remains in place on the patient connector, thereby sealing the connector.

Single coupling connection of the disclosed device to the patient connector ensures passive connector scrubbing action, in compliance with Society for Healthcare Epidemiology of America (SHEA) and Infusion Nurses Standards (INS) guidelines, followed by IV-line flushing. The disclosed device enhances compliance with nursing disinfection guidelines, reduces touch contamination by promoting an aseptic, no touch, passive scrubbing technique, reduces microbial growth against those microbes commonly associated with CRBSI and simplifies workflow. By incorporating passive scrubbing, disinfection capability within the disinfection cap of the device, intermediate the flushing fluid flow path from the syringe to the patient connector, clinicians will not need to remember whether the patient connector/hub has been scrubbed prior to coupling the flush syringe to the IV connector. Thereafter, if the disclosed device, is used solely for intermitting flushing prior to administration of drugs or other fluids through the patient connector, the disinfection cap is selectively removed to allow drug infusion through the patient connector. Alternatively, if the disclosed device was used for final patient connector flushing after drug administration, the housing and flush syringe are separated from the disinfection cap, leaving the cap in place on the patient connector. In practice, when performing a SAS workflow process, it is possible to administer one or more drugs through a patient connector with only two devices of the present disclosure. The first device scrubs and flushes the patient connector; then one or more drugs is/are administered through the now scrubbed/flushed patient connector. Thereafter, the second device performs the final scrub and flush and leaves its disinfection cap in situ on the patient connector. SASH workflow requires a third one of the disinfection/flushing devices of the present disclosure to perform the final heparin flush of the patient connector.

One aspect of the present disclosure pertains to a device for both disinfecting and flushing of an intravenous patient connector in only one device connection. The device includes a guide housing having an internal, first, circumferential wall surface. The guide housing has a proximal end wall defining a first through aperture therein, and a distal end wall defining second through aperture. The housing has a first internal cavity defined within the first circumferential wall surface and the respective proximal and distal end walls. The device further includes an end cap captured within and translatable within the first internal cavity. A proximal end of the end cap defines an inlet and a first Luer connector adapted for engagement, through the first through aperture of the housing, with a corresponding Luer tip of a flush syringe. The distal end of the end cap defines a shaft with a spiked tip. The shaft defines an outlet and an internal lumen in fluid communication with the inlet and the outlet of the end cap. The device further includes a disinfection cap having an internal, second, circumferential wall surface, a proximal end wall defining a third through aperture for receipt of the shaft of the end cap, and a distal open end. The second circumferential wall surface defines a second Luer connector adapted for engagement with a corresponding Luer connector of an IV patient connector. The respective first and second cavities are aligned with each other so that the spiked tip of the end cap is translatable within the third through aperture into the second cavity of the disinfection cap. An elastomeric sleeve is captured within the second internal cavity. The sleeve has a proximal surface that is pierced by the spiked tip when the end cap shaft is translated through the third through aperture, and a distal surface facing the open distal end of the disinfection cap. A disinfection pad is captured within the second internal cavity, intermediate the elastomeric sleeve and the distal open end of the disinfection cap. The disinfection pad defines a fourth aperture for exposure of the distal surface of the elastomeric sleeve to the distal open end of the disinfection cap. The disinfection pad also defines a distal end surface adapted for disinfection of a corresponding patient IV connector when the disinfection cap is coupled to a connector. In some embodiments, a pre-filled flush syringe is coupled to the first Luer connector of the end cap. In device operation, the coupled flush syringe is advanced into the housing, causing translation of the spiked tip of the end cap into the disinfection cap, which in turn pierces the elastomeric sleeve and enables direct fluid communication of flushing solution contained within the coupled syringe between the inlet of the end cap and the distal open end of the disinfection cap, and in turn into the coupled patient connector.

Another aspect of the present disclosure pertains to a system for disinfecting and flushing an intravenous patient connector in only one device connection. The system includes a guide housing having an internal, first, circumferential wall surface, a proximal end wall defining a first through aperture therein, a distal end wall defining second through aperture therein, and a first internal cavity defined within the first circumferential wall surface and the respective proximal and distal end walls. An end cap is captured within and translatable within the first internal cavity of the housing. A proximal end of the end cap defines an inlet and a first Luer connector. The corresponding distal end of the end cap defines a shaft with a spiked tip. The shaft defines an outlet and an internal lumen in fluid communication with the inlet and the outlet of the end cap. The system includes a disinfection cap having an internal, second, circumferential wall surface, a proximal end wall defining a third through aperture for receipt of the shaft of the end cap, and a distal open end. The second circumferential wall surface defines a second Luer connector. The respective first and second cavities are aligned with each other so that the spiked tip of the end cap is translatable within the third through aperture into the second cavity. An elastomeric sleeve is captured within the second internal cavity. The sleeve has a proximal surface that is pierced by the spiked tip when the end cap shaft is translated through the third through aperture, and a distal surface facing the open distal end of the disinfection cap. A disinfection pad is captured within the second internal cavity of the disinfection cap, intermediate the elastomeric sleeve and the distal open end of the disinfection cap. The pad defines a fourth aperture for exposure of the distal surface of the elastomeric sleeve to the distal open end of the disinfection cap. The disinfection pad defines a distal end surface. The system includes a pre-filled flush syringe having a syringe barrel containing a flushing solution, a translatable plunger within the syringe barrel, and a third Luer connector that is inserted through the first through aperture of the guide housing and coupled to the first Luer connector of the end cap. The inlet of the end cap is in fluid communication with the flushing solution contained within the syringe barrel. The system further includes a patient connector having a connector body defining a fourth Luer connector that is coupled to the second Luer connector within the disinfection cap, with the distal end surface of the disinfection pad in contact with the fourth Luer connector. Advancement of the flush syringe into the first cavity translates the spiked tip of the end cap, piercing the elastomeric sleeve and enabling fluid communication and flow of the flushing solution from the flushing syringe through the patient connector, via the inlet, internal lumen and outlet of the end cap. Advancement of the syringe plunger dispenses the flushing solution into the patient connector.

In some embodiments, after the patient connector is flushed with the flush syringe that is coupled to the housing, both the syringe and the housing portion of the device are selectively decoupled from the disinfection cap portion of the device by releasing a selectively engageable locking mechanism. Upon release of the housing from the disinfection cap, the latter remains in place to seal the patient connector and avoid exposure of the connector end surface and its lumen to the environment. In other embodiments, the entire device cap and housing, along with the flush syringe that is coupled to the housing, are selectively decoupled from the patient connector, for further patient drug administration and the like. In some device embodiments, the locking mechanism facilitates selective removal of the entire device and attached flush syringe from the patent port or only removal of the housing and syringe, leaving the disinfection cap affixed to the patient connector. In other device embodiments, the locking mechanism only allows removal of the housing and syringe. In yet other device embodiments, the disinfection cap and the housing are permanently coupled to each other; the entire device, as well as the flush syringe, are removed by decoupling the disinfection cap from the IV patient connector.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
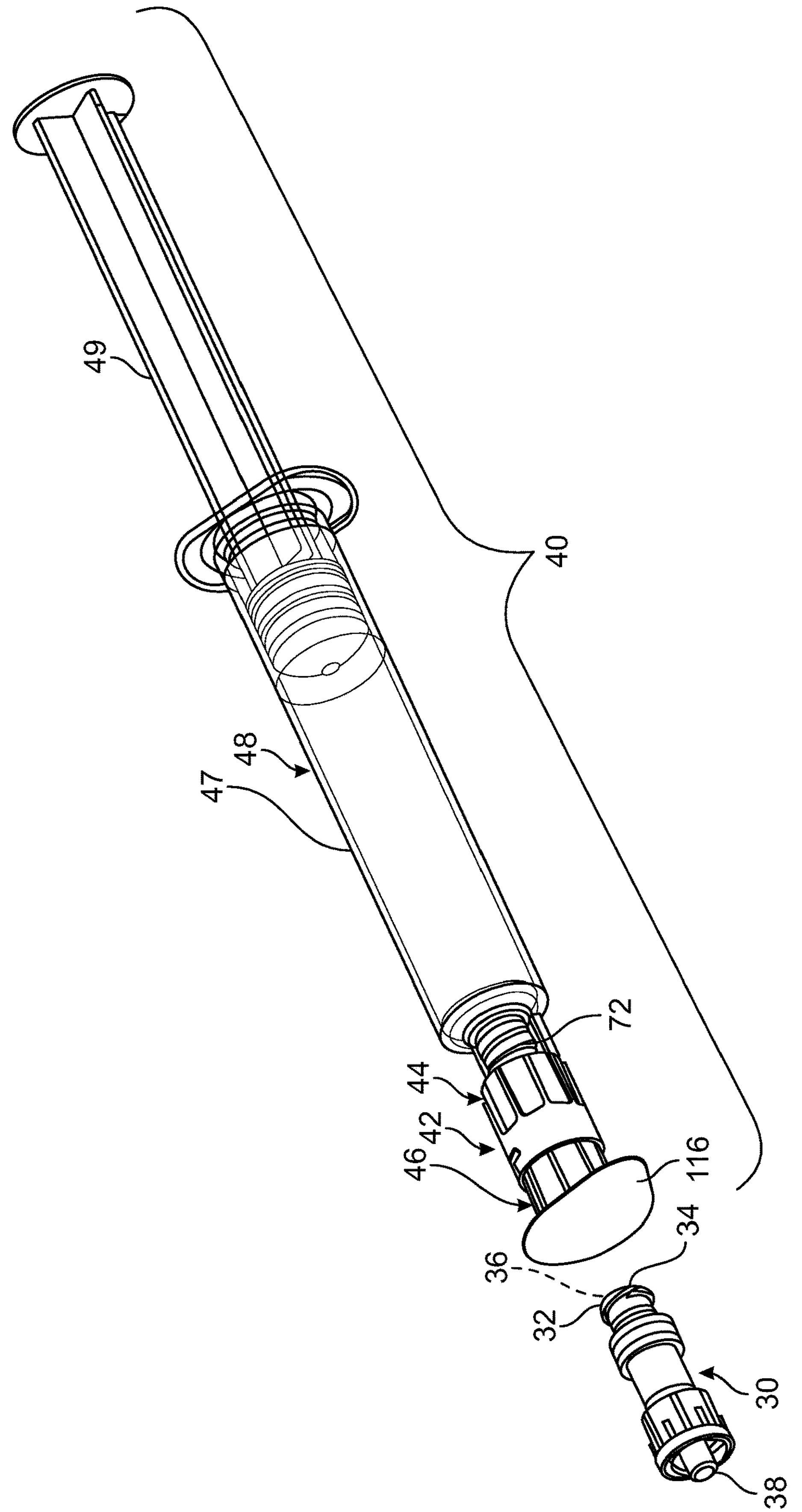
FIG. 1 is an isometric view of an embodiment of a disinfection and flushing device of the present disclosure, prior to removing a web peel lid seal and coupling a disinfection cap portion of the device to an exemplary IV connector of a medical patient.

The patient connector disinfection and flushing device of the present disclosure requires only a single coupling of a disinfection cap of the device to the IV patient connector, both to scrub the patient connector and to administer flushing solution through the connector via a flush syringe that is already coupled to a housing portion of the device. The disinfection cap and housing portions of the device are coupled together during the initial patient connector scrub and flush operation. Thereafter, in some embodiments, the housing and its attached, spent flush syringe, are selectively separable from the disinfection cap portion of the device, so that the disinfection cap remains in place on the patient connector. In other embodiments, the entire device, including the disinfection cap, the housing, and the separately coupled flush syringe are disconnected from the patient connector, so that drugs can be administered through the connector. Optionally, after drug administration, a second device of the present disclosure is utilized to provide a final scrubbing and flushing of the patient connector; whereupon after separation of its guide housing and spent flush syringe, its disinfection cap remains in place on the patient connector.

In this disclosure, a convention is followed wherein the distal end of a device is the end closest to a patient, e.g., for delivery of one or more drugs to the patient, and the proximal end of the device is the end away from the patient and closest to a clinician or other medical practitioner. With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a patient connector, catheter or IV line.

As used herein, the term "Luer connector" refers to a connection collar of a medical device (e.g., a VAD) that is the standard way of attaching needleless patient connectors, syringes, catheters, hubbed needles, IV tubes, etc. to each other. The Luer connector comprises male and female interlocking tubes, slightly tapered to hold together better with even just a simple pressure/twist fit. Threaded Luer connectors include an additional outer rim of threads, allowing them to be more secure. The Luer connector male end is generally associated with a flush syringe and can interlock and connect to the female end located on the patient connector (including by way of non-limiting example a needleless patient connector) or other type of vascular access device (VAD). A Luer connector comprises a distal end, a proximal end, an irregularly shaped outer wall, a profiled center passageway for fluid communication from the chamber of the barrel of a syringe to the patient connector or other type of hub of a vascular access device. (VAD). A Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard Luer connector increases from the open distal end to the proximal end. A female standard Luer connector decreases from the open proximal end to the distal end. According to ISO 80369-7:2016, a male standard Luer connector has an outer cross-sectional diameter measured 0.75 mm from the distal end of the tip of between 3.970 mm and 4.072 mm. The length of the male standard Luer taper is between 7.500 mm to 10.500 mm. The outer cross-sectional diameter measured 7.500 mm from the distal end of the tip is between 4.376 mm and 4.476 mm. As used herein, the phrases "male standard Luer connector" and "female standard Luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually or to require specific spatial orientations, to implement various aspects of the embodiments of the present disclosure.

According to still further exemplary implementations of the embodiments of the present disclosure, a needleless connector-type patient connector or other medical device to be cleaned may comprise female threads that are sized and have a thread pattern that will engage with a standard ISO 594-2 type of male fitting and/or male threads that are sized and have a thread pattern that will engage with a standard ISO 594-2 type of female fitting. An example of an ISO 594-2 type of fitting is a Q-style fitting.

In one or more embodiments, a female connector-type, patient connector or other medical device to be cleaned may be selected from the group consisting essentially of: needle-type connectors (for direct injection into a patient or insertion into a drug vial for aspiration of a drug dose therefrom), needle-free connectors, catheter Luer connectors, stopcocks, and hemodialysis connectors. In one or more embodiments, the needleless connector is selected from a Q-Syte™ connector, MaxPlus™ MaxPlus Clear™, MaxZero™, UltraSite®, Caresite®, In Vision-Plus™, Safeline®, One-Link™, V-Link™, ClearLink™, NeutraClear™, Clave®, MicroClave®, MicroClave Clear®, Neutron™, NanoClave@, Kendall™, *Nexus*®, In Vision®, Vadsite™, Bionector®, etc.

Before describing exemplary embodiments of the disclosure, it is to be understood that the disclosure is not limited to the details of construction or process steps set forth in the following description. The patient connector disinfection and flushing concepts of this disclosure are capable of being implemented in other embodiments and of being practiced or being conducted in many ways.

The following non-limiting examples demonstrate principles according to one or more embodiments of the disclosure. In the FIGS. 1-20, an exemplary patient connector 30 is a valve-type, needle-free connector (NFC). A proximal end of the patient connector 30 incorporates a threaded Luer connector 32, which defines a proximal axial face 34 and an internal passageway 36 for communication with a downstream IV line or other VAD (not shown in the figures) coupled to the distal end 38 of the connector. The threaded Luer connector 32 is disinfected and flushed with one or more embodiments of disinfection and flushing devices disclosed herein. After cleaning and flushing the patient connector 30, a healthcare provider thereafter may administer one or more drugs to the patient, typically disinfecting the connector before and after each new syringe coupling thereto. After administration of the last drug to the patient, the care provider typically disinfects and flushes the patient connector 30 again prior to attachment a cap to its threaded Luer connector 32.

Figure 2:
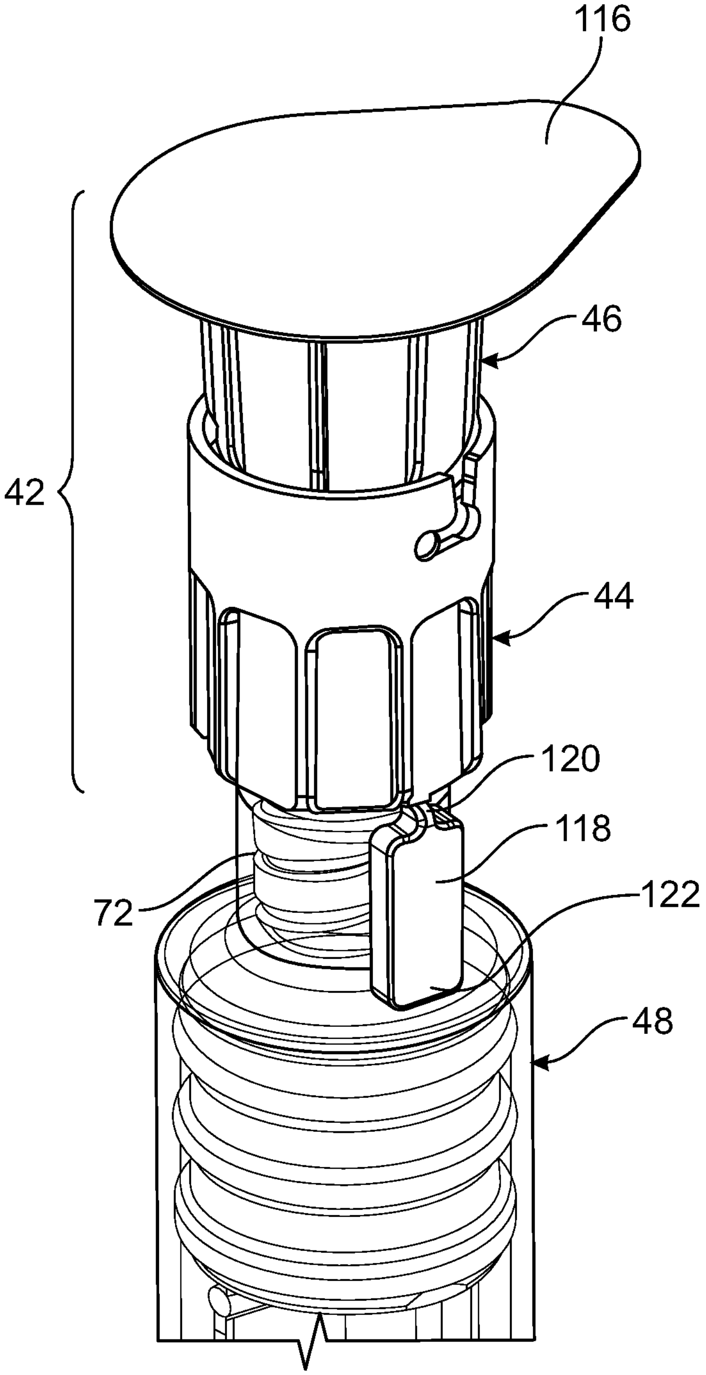
FIG. 2 is an isometric view of the distal end of the device of FIG. 1.
Figure 3:
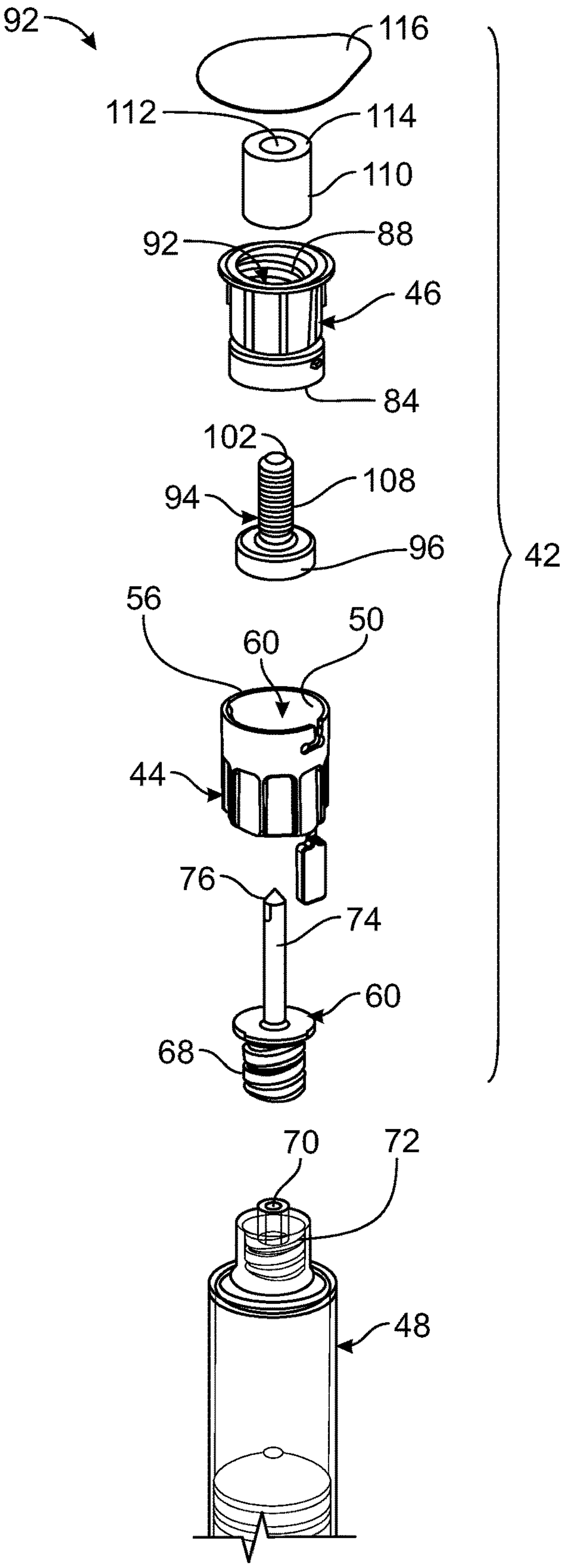
FIG. 3 is an exploded view of the device of FIG. 1.

Referring now to FIGS. 1-8 of the drawings, a first aspect or embodiment of the present disclosure is a system 40 for disinfecting and flushing an intravenous patient connector 30. As shown in FIGS. 1-3, system 40 includes device 42 for disinfecting and flushing the intravenous patient connector. Externally visible components of device 42 comprise a guide housing 44 and a disinfection cap 46. System 40 also includes a flush syringe 48 that is coupled to the guide housing 44 of the device 42. The flush syringe 48 includes a syringe barrel 47 containing the flushing solution, and a translatable plunger 49. In some embodiments, a sterilized device 42 is separately packaged for coupling with a separate sterile flush syringe 48 (pre-filled or filled on site) prior to patient administration. In other embodiments, the sterilized device 42 and a pre-filled flush syringe 48 are coupled during manufacture and shipped in sterile packaging, for patient administration by a healthcare provider.

FIGS. 2-5 illustrate internal components of the device 42. The guide housing 44 has an internal, first, circumferential wall surface 50, a proximal end wall 52 defining a first through aperture 54 therein, a distal end wall 56 defining second through aperture 58 therein, and a first internal cavity 60 defined within the first circumferential wall surface and the respective proximal and distal end walls. An end cap 62 is captured within and translatable within the first internal cavity 60 of the guide housing 44. A proximal end 64 of the end cap 62 defines an inlet 66 and a first Luer connector 68 for coupling to a corresponding Luer tip 70 and threaded Luer connector 72 of the syringe 48. The first Luer connector 68 effectively allows the end cap 62 to substitute for known needleless guides that are typically utilized with known flushing syringes. Thus, the end cap 62 of the device 42 is compatible for use with known flush syringe designs. The distal end of the end cap 62 defines a shaft 74 with a spiked tip 76. The shaft 74 is hollow, defining an internal lumen 78 that is in fluid communication with the inlet 66 and the outlet 80 of the end cap 62. The threaded coupling of the first Luer connector 68 and the corresponding threaded Luer connector 72 mutually couples the syringe 48 and the guide housing 44. This establishes a fluid path for discharge of the saline flushing solution contained within the syringe barrel 47, respectively through the Luer tip 70, the inlet 66, the internal lumen 78 and the outlet 80 of the end cap 62, in turn through the disinfection cap 46 and into the patient connector 30.

In summary, the guide housing 44 functions as an enclosure to restrain the end cap 62 therein, to guide translation of the end cap within the first internal cavity 60, and to prevent inadvertent piercing of the elastomeric sleeve 94 by the spiked tip 76 before intended flushing of the patient connector 30. The guide housing 44 structure enables it to be coupled to the disinfection cap 46.

The disinfection cap 46 has an internal, second, circumferential wall surface 82. An inserted, annular-shaped, proximal end wall 84 of the disinfection cap 46 defines a third through aperture 86 for receipt of the shaft 74 of the end cap 62. The disinfection cap 46 has distal open end 88 for receipt of the patient connector 30; its second circumferential wall surface 82 defines a second Luer connector 90 for coupling to the corresponding threaded Luer connector 32 of the patient connector. A second internal cavity 92 is defined within the second circumferential wall surface 82, the proximal end wall 84 and the distal open end 88 of the disinfection cap 46.

Figure 4:
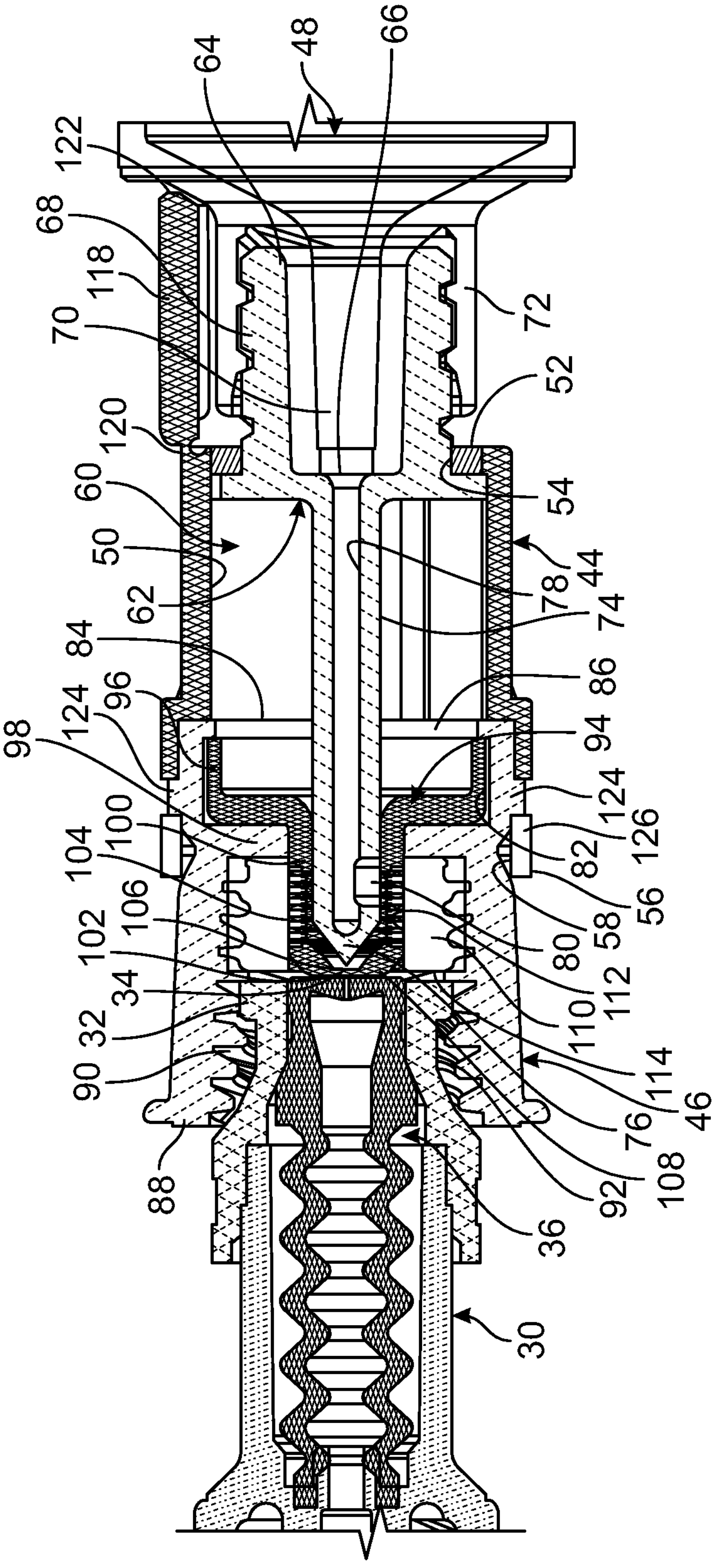
FIG. 4 is an axial, cross-sectional view of the device of FIG. 1, after coupling the disinfection cap portion thereof to an exemplary IV connector, prior to advancement of the flush syringe into engagement with the IV connector.
Figure 5:
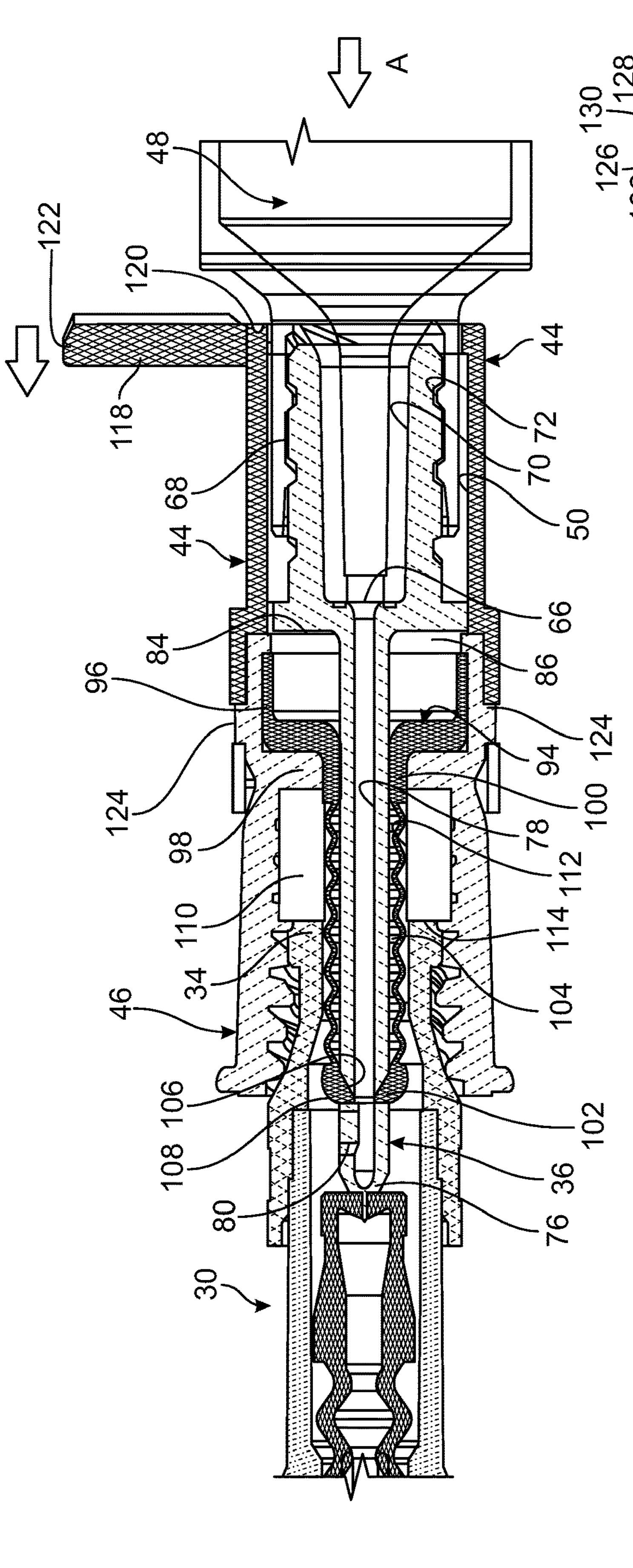
FIG. 5 is an axial cross-sectional view of the device of FIG. 4, after coupling the disinfection cap portion thereof to the exemplary IV connector, and after advancement of the flush syringe into engagement with the IV connector.

The disinfection cap 46 and the guide housing 44 are slidably coupled to each other in nested fashion; when nested, the respective first 60 and second 92 cavities are aligned with each other, so that the spiked tip 76 of the end cap 62 is translatable within the third through aperture 86 into the second cavity. While the embodiment of FIGS. 4 and 5 show the disinfection cap 46 nested within the guide housing 44, in other embodiments the nested orientation is reversed: the guide housing is nested within the disinfection cap. While this embodiment also shows axial symmetry between the guide housing 44 and the disinfection cap 46, with concentric end cap 62 alignment, in other embodiments they are axially asymmetrical.

An elastomeric sleeve 94 is captured within the second internal cavity 92 of the disinfection cap 46, which functions as a pierceable, resealable septum for the cap. The elastomeric sleeve 94 has a peripheral flange 96 that is captured between the proximal end wall 84 and an annular internal bushing 98 of the disinfection cap 46. The elastomeric sleeve 94 has a tubular stem portion 100 that projects into the distal portion of the second internal cavity 92, for receiving the shaft 74 and the spiked tip 76 of the end cap 62. A corresponding distal tip 102 of the tubular stem portion 100 is pierceable by the spiked tip 76. The tubular stem portion 100 of the elastomeric sleeve 94 includes an axially expandable bellows 104, which extends axially upon insertion therein of the shaft 74 of the end cap 62. Comparing FIGS. 4 and 5, the proximal surface 106 of the elastomeric sleeve 94 is pierced by the spiked tip 76 when the shaft 74 of the end cap 62 is translated through the third through aperture 86 of the disinfection cap 46 and the internal bushing 98, as shown by the arrow A. Distal surface 108 of the elastomeric sleeve 94 faces the distal open end 88 of the disinfection cap 46.

During assembly of the disinfection cap 46, elastomeric sleeve 94 is inserted into the second internal cavity 92 from the proximal end 64 of the cap, with the tubular stem portion 100 passing through a center aperture of the internal bushing 98. Next, the annular, proximal end wall 84 is inserted into the second internal cavity, capturing the sleeve's peripheral flange 96.

Components of the disinfection and flushing device 42, and the other embodiments described herein, are constructed by injection molding or vacuum thermal forming. Exemplary materials used to construct the guide housing 44, the disinfection cap 46 and the end cap 62 include thermoplastic polymers. The elastomeric sleeve 94 is constructed by compression molding of cross-linked rubber or thermoplastic elastomer materials. An exemplary hardness range for the elastomeric sleeve is 25-100 Shore A, and more particularly 45-80 Shore A. Generally, the components of the disinfection and flushing device 42 are constructed with types of medical grade, plastic materials such as polycarbonate, polypropylene, polyethylene, glycol-modified polyethylene terephthalate, acrylonitrile butadiene styrene or any other moldable plastic material used in medical devices.

As illustrated in FIGS. 2, 4, 5 and 8, a disinfection pad 110 is captured within the second internal cavity 92, intermediate the elastomeric sleeve 94 and the distal open end 88 of the disinfection cap 46. The disinfection pad 110 defines a fourth aperture 112 for exposure of the distal surface 108 of the elastomeric sleeve 94 to the distal open end 88 of the disinfection cap 46. The disinfection pad 110 defines a distal end surface 114 that contacts at least the distal end surface 38 of the patient connector 30 when the disinfection cap is affixed or otherwise coupled to the patient connector. In some embodiments, the disinfection pad 110 compresses upon affixation of the disinfection cap 46 to a patient connector 30. In some embodiments, the disinfection pad 110 further comprises an antimicrobial material and/or is impregnated with an antimicrobial agent. More particularly, in some embodiments, the disinfection pad 110 is a disinfectant sponge or other alternative absorbent material retained within the disinfection cap 46. In some embodiments, the disinfection pad 110 includes an absorbed or infiltrated, liquid or gel, disinfectant or an antimicrobial agent for disinfecting the patient connector 30 or other medical device that is to be cleaned with the disinfection cap 46. In one or more embodiments, the absorbent material comprising the disinfection pad 110 is a nonwoven material, foam, or a sponge having a porous structure. In a specific embodiment, the foam is a polyurethane foam. In a specific embodiment, the absorbent material is a sponge.

The disinfection pad 110 retains disinfectant or antimicrobial agent in its porous structure due to surface tension and releases disinfectant or antimicrobial agent when squeezed or compressed by contact with the patient connector 30 or other medical device that is to be cleaned by the disinfection cap 46. The disinfection cap 46 is compatible in interacting with various disinfectants. In one or more embodiments, the disinfectant or antimicrobial agent includes variations of alcohol or chlorhexidine. In one or more embodiments, the disinfectant or antimicrobial agent is selected from the group consisting essentially of isopropyl alcohol, ethanol, 2-propanol, butanol, methylparaben, ethyl paraben, propylparaben, propyl gallate, butylated hydroxy anisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel. In one or more specific embodiments, the disinfectant or antimicrobial agent is 70% isopropyl alcohol (IPA). As shown in FIGS. 4 and 5, the elastomeric sleeve 94 functions as a seal for preventing disinfectant or antimicrobial agent (e.g., IPA) leakage into the patient connector 30 before and during mutual connection of the patient connector and the disinfection cap 46. The self-sealing, distal tip 102 of the elastomeric sleeve 94 also seals the disinfection cap 46 after syringe withdrawal, which prevents IPA leakage and exposure of the patient connector 30 to the non-sterile, external environment.

As the disinfection cap 46 is coupled to the patient connector 30, cap rotation needed to mate thread engagement between the corresponding threaded Luer connectors 32 and 90 ensures sufficient scrubbing of the connector, in compliance with Infusion Nurses Standards (INS) guidelines. The threaded engagement process also establishes a leak proof connection between the disinfection cap 46 and the patient connector 30.

Web peel lid 116 covers the distal open end 88 of the disinfection cap 46. In other embodiments, the device does not include a web peel lid covering the distal open end of the inspection cap. In one or more embodiments, the web peel lid 116 is a peelable seal, which comprises an aluminum or multi-layer polymer film peel back top. The web peel lid 116 minimizes entry of potential particulate hazard and also provides a substantially impermeable enclosure for the distal open end 88 of the disinfection cap 46, provides leak prevention and protection of the second internal cavity 92 that is formed within the disinfection cap, protects the absorbed, infiltrated contents of the disinfection pad 110 or other disinfectant media contained within the second internal cavity, and/or maintains a sealed, sterilized environment within the disinfection cap. Seal composition of the web peel lid 116 provides a sufficient environmental seal between its aluminum or polymer film and the disinfection cap's distal open end 88 at a range of temperatures, pressures, and humidity levels expected within a medical treatment facility. In some embodiments, the web peel lid 116 is heat-sealed or induction-sealed to the distal open end 88 of the disinfection cap 46. In other embodiments, the web peel lid 116 is scaled to the distal open end 88 of the disinfection cap 46 with pressure or thermally sensitive adhesive.

The guide housing 44 has a pivoting guide housing lid 118 to block inadvertent advancement translation of the syringe 48 and the end cap 62 within the guide housing's first internal cavity 60. A distal end 120 of the guide housing lid 118 is pivotally coupled to the guide housing 44. As depicted in FIG. 4, proximal end 122 of the guide housing lid 118 projects axially away from the proximal end wall 52 of the housing in a first position, in opposed orientation with the syringe 48. When the guide housing lid 118 is in its first position, it blocks advancement of the syringe 48 and the mutually coupled end cap 62; this prevents the coupled, spiked tip 76 of the end cap 62 from piercing the distal tip 102 of the tubular stem portion 100 of the elastomeric sleeve 94. Before a healthcare flushes the patient connector 30, the guide housing lid 118 is pivoted and displaced laterally away from the guide housing 44, in a second position shown in FIG. 5, where it no longer blocks advancement of the syringe 48 within the first internal cavity 60 of the guide housing 44. Upon advancement of the syringe 48 the spiked tip 76 of the end cap 62 pierces the distal tip 102 of the elastomeric sleeve 94.

As previously described, the disinfection cap 46 and the guide housing 44 are slidably coupled to each other in nested fashion. In some embodiments, the slidably coupled guide housing and disinfection cap are coupled together with a locking mechanism. In the device embodiment 42 of FIGS. 1-8, the locking mechanism facilitates selective retention of the disinfection cap 46 on the patient connector 30 while removing the guide housing 44 and the spent syringe 48.

Figure 6:
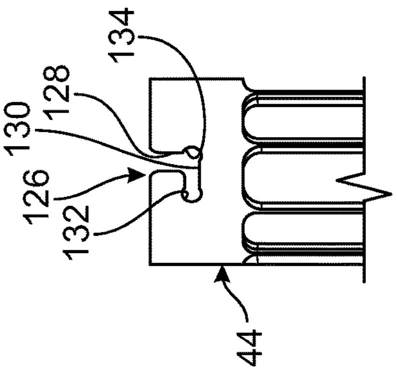
FIG. 6 is a detailed elevational view of a portion of the twist-lock, locking engagement mechanism of the embodiment of the device of FIG. 1 that selectively couples the disinfection cap to the housing of the device.

The locking mechanism in FIGS. 1-8 is a twist-lock, bayonet-type, locking mechanism comprising two pairs of mutually engaging, radially-outwardly projecting, bayonet pins 124 and female receptor slots 126 that are circumferentially spaced in 180-degree, opposed orientation. Referring to FIG. 6, each female receptor slot 126 has an L-shaped profile, comprising an axially aligned, first slot segment 128 and a transversely aligned, second slot segment 130. In one or more alternate embodiments, each female receptor slot 126 has a T-shaped profile or a J-shaped profile. The lateral ends of the second slot segment 130 terminate in first 132 and second 134 necked serifs that retain the corresponding bayonet pin 124. The bayonet pin 124 is engaged within the first serif 132 when the second Luer connector 90 of the disinfection cap 46 portion of the entire assembled disinfection and flushing system 40 is engaged in threaded fashion upon the corresponding, threaded Luer connector 32 of the patient connector 30. Conversely, when the entire coupled guide housing 44, disinfection cap 46 and flush syringe 48 are to be removed from the patient connector 30, bayonet pin 124 is engaged within the second serif 134.

Figure 7:
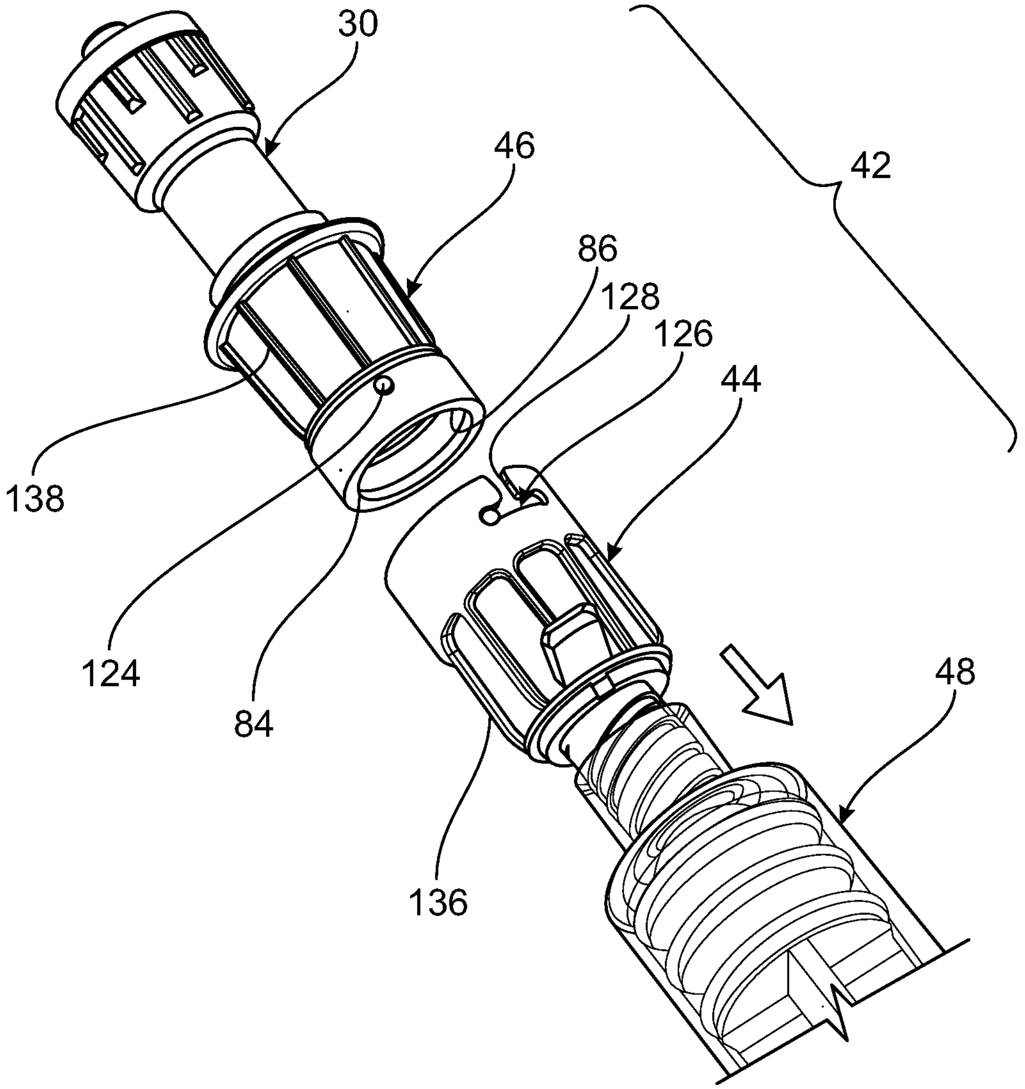
FIG. 7 is an isometric view of the device of FIGS. 1-6, after selective separation of the housing portion of the device and its attached flush syringe from the disinfection cap portion of the device.
Figure 8:
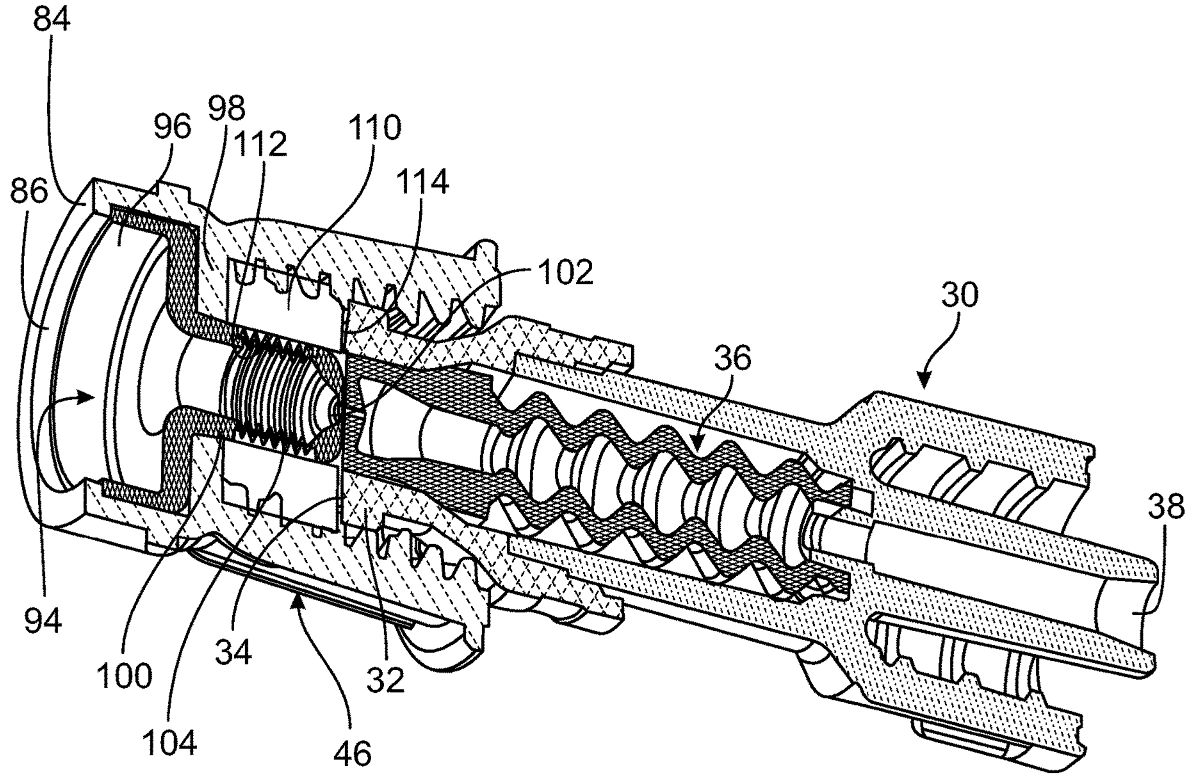
FIG. 8 is an axial cross-section of the disinfection cap portion of the device of FIG. 7 remaining coupled to the IV patient connector, after selective separation of the device housing.
Figure 9:
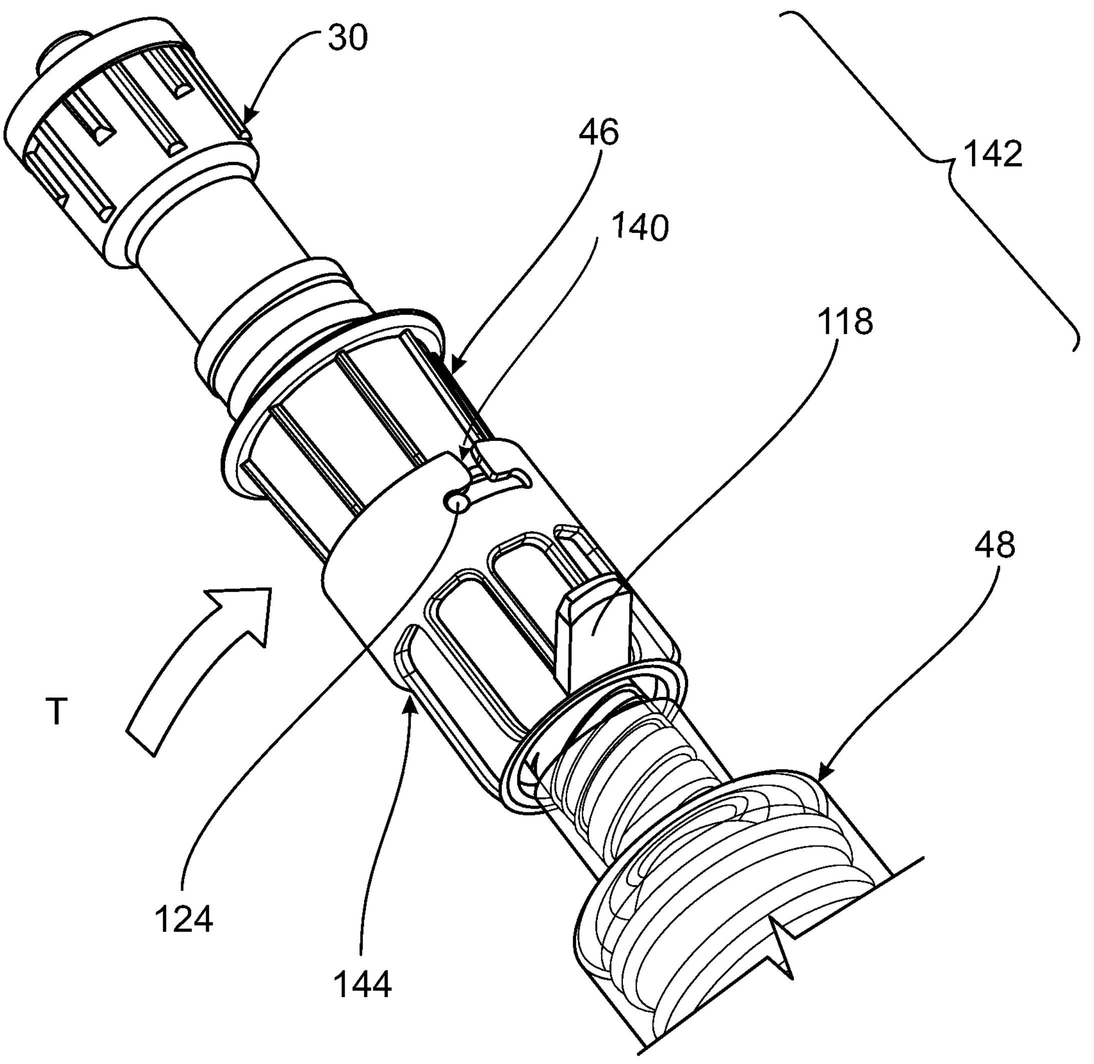
FIG. 9 is an isometric view of a second embodiment of a disinfection and flushing device of the present disclosure after coupling of its disinfection cap portion to an exemplary IV connector of a medical patient and prior to advancement of the flush syringe into engagement with the IV connector.
Figure 10:
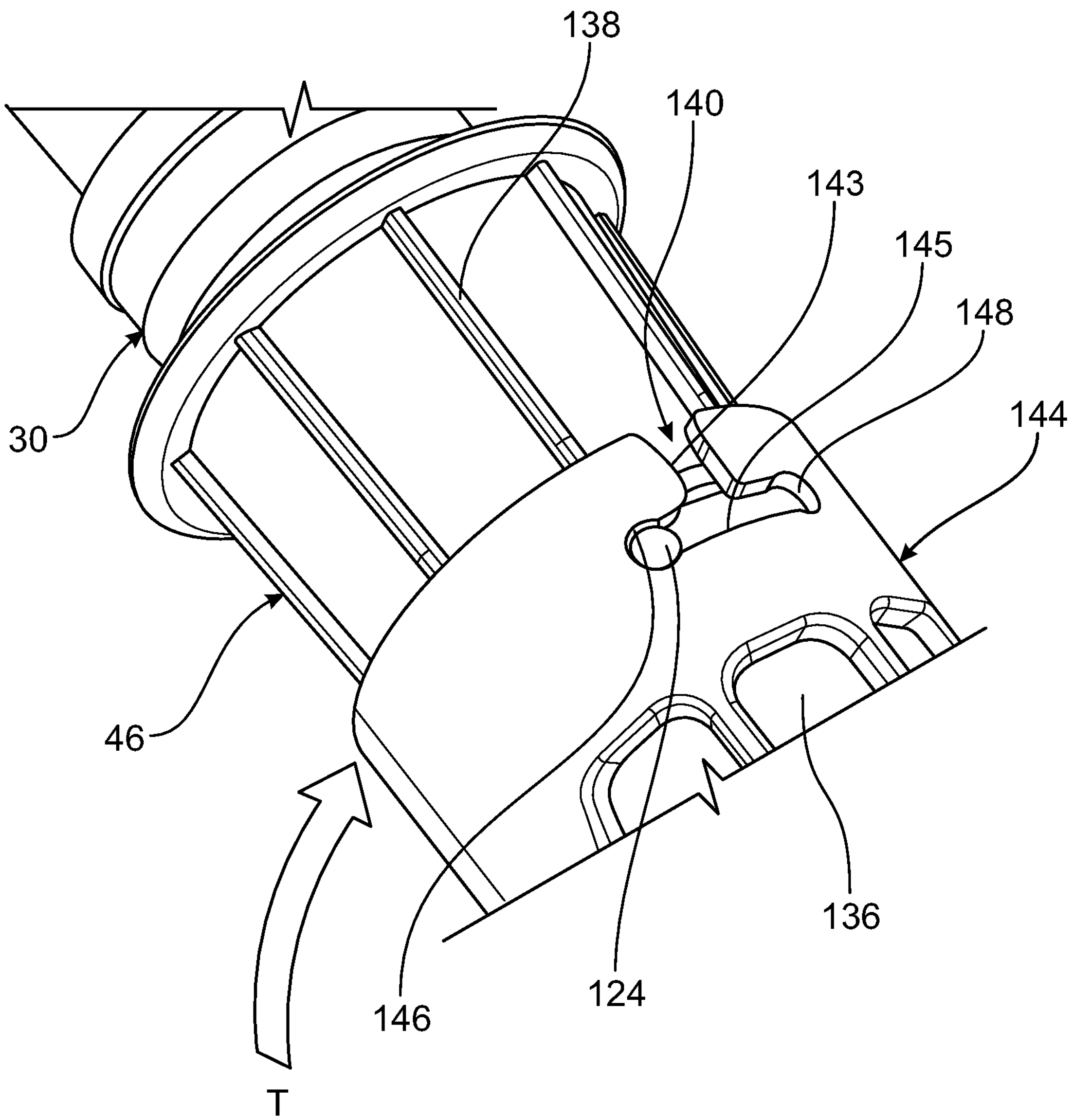
FIG. 10 is an enlarged, isometric view of a portion of the twist-lock, locking engagement mechanism of the embodiment of the device of FIG. 9 that selectively couples the disinfection cap to the housing of the device.
Figure 11:
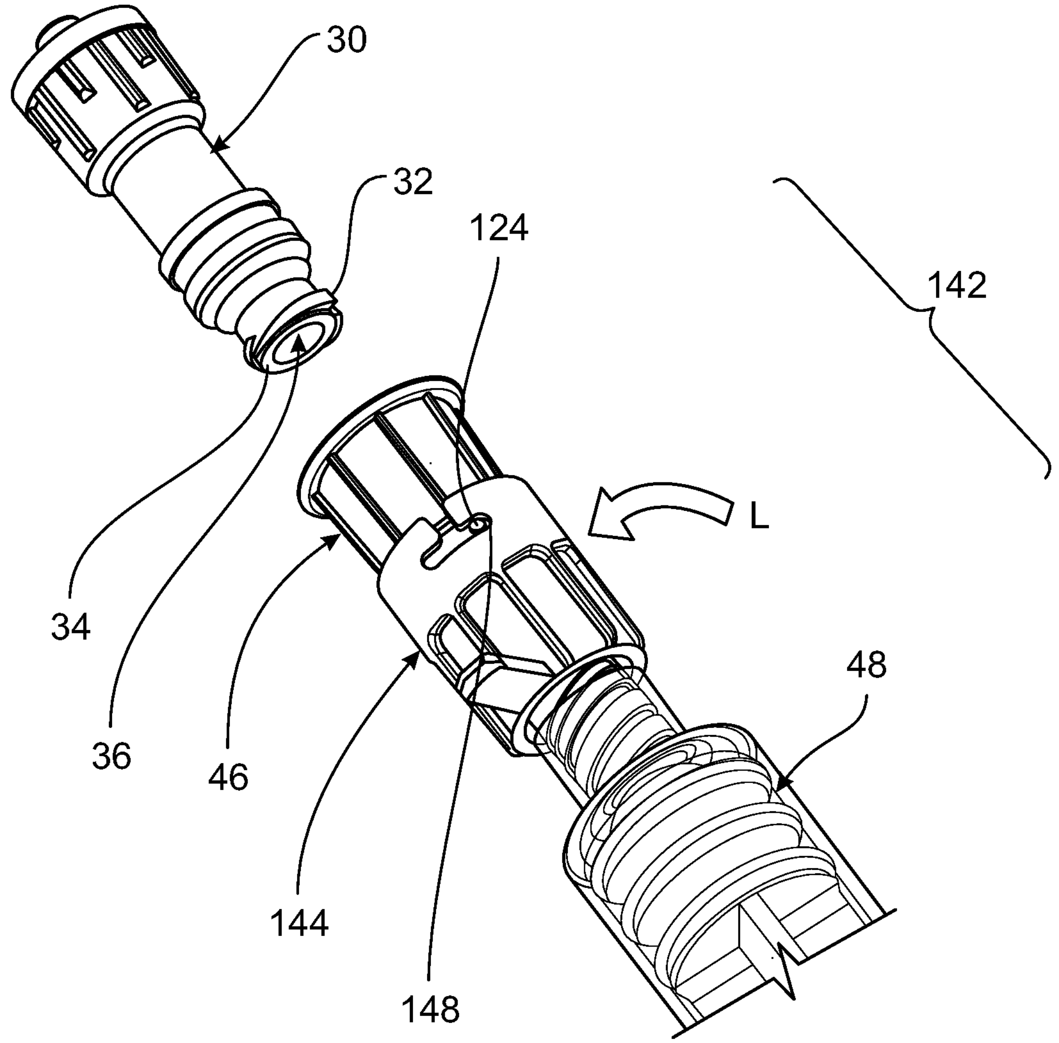
FIG. 11 is an isometric view of the device of FIGS. 9 and 10, after selective separation of the entire device and its attached flush syringe from the IV patient connector.

As shown in FIGS. 7 and 8, when the guide housing 44 and the disinfection cap 46 are rotated relative to each other so that the bayonet pin 124 is oriented in alignment with the axially aligned, first slot segment 128, the housing and cap are axially separable from each other, allowing separation and withdrawal of the guide housing and the flush syringe 48 from the patient connector 30, while leaving the disinfection cap coupled to the patient connector. During separation and withdrawal, the syringe 48 is retracted out of the guide housing 44, separating the spiked tip 76 and outlet 80 of the end cap 62 from the elastomeric sleeve 94 of the disinfection cap 46, and thereby isolating the sterile patient connector 30 from the non-sterile outside environment. To facilitate twisting rotation of the system 40 components relative to each other, external grasping fins 136 are oriented on the guide housing 44 and external grasping fins 138 are oriented on the disinfection cap 46.

In some embodiments, a single, mutually paired, engaging bayonet pin 124 and female receptor slot 126 is incorporated in the locking mechanism. In other device embodiments, the locking mechanism comprises more than two pairs of mutually engaging pins and receptor slots. In some embodiments, the bayonet pins are oriented on the guide housing while the receptor slots are oriented in the disinfection cap.

Figure 12:
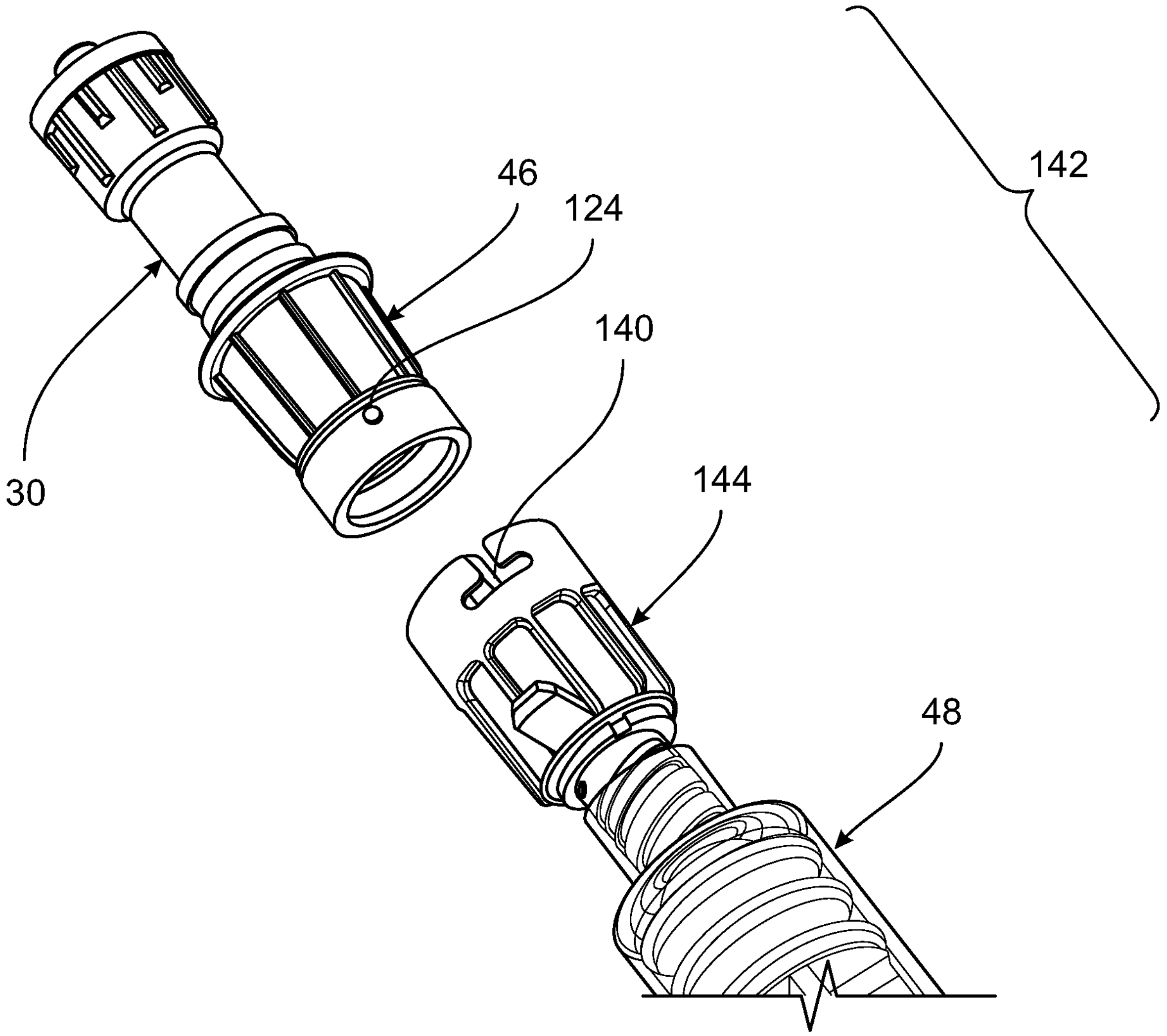
FIG. 12 is an isometric view of the device of FIGS. 9 and 10, after selective separation of the housing portion of the device and its attached flush syringe from the disinfection cap portion of the device, with said cap remaining coupled to the patient connector.

FIGS. 9-12 depict a disinfection and flushing device 142 with a second, twist-lock, bayonet-type, locking-mechanism embodiment that facilitates selective retention of the disinfection cap 46 on the patient connector 30. The remainder of the structural components of the system and their operation correspond to those of the system 40 of FIGS. 1-8. The second embodiment of twist-lock mechanism comprises a bayonet pin 124 on the disinfection cap 46 and a T-shaped receptor slot 140 formed in the guide housing 144. The T-shaped receptor slot 140 comprises an axially aligned, third slot segment 143 and a transversely aligned fourth slot segment 145. The lateral ends of the fourth slot segment 145 terminate in third 146 and fourth 148 necked serifs that retain the corresponding bayonet pin 124. The bayonet pin 124 is engaged within the third serif 146 when the second Luer connector 90 of the disinfection cap 46 portion of the entire assembled disinfection and flushing system is engaged in threaded fashion and tightened upon the corresponding, threaded Luer connector 32 of the patient connector 30 (see arrow T of FIGS. 9 and 10). Conversely, when the entire coupled guide housing 144, disinfection cap 46 and flush syringe 48 are to be removed from the patient connector 30, bayonet pin 124 is engaged within the fourth serif 148 (see arrow L of FIG. 11). As shown in FIG. 12., when the guide housing 144 and the disinfection cap 46 are rotated relative to each other so that the bayonet pin 124 is oriented in alignment with the axially aligned, fourth slot segment 145, the housing and cap are axially separable from each other, allowing separation and withdrawal of the guide housing and the flush syringe 48 from the patient connector 30, while leaving the disinfection cap coupled to the patient connector.

Figure 13:
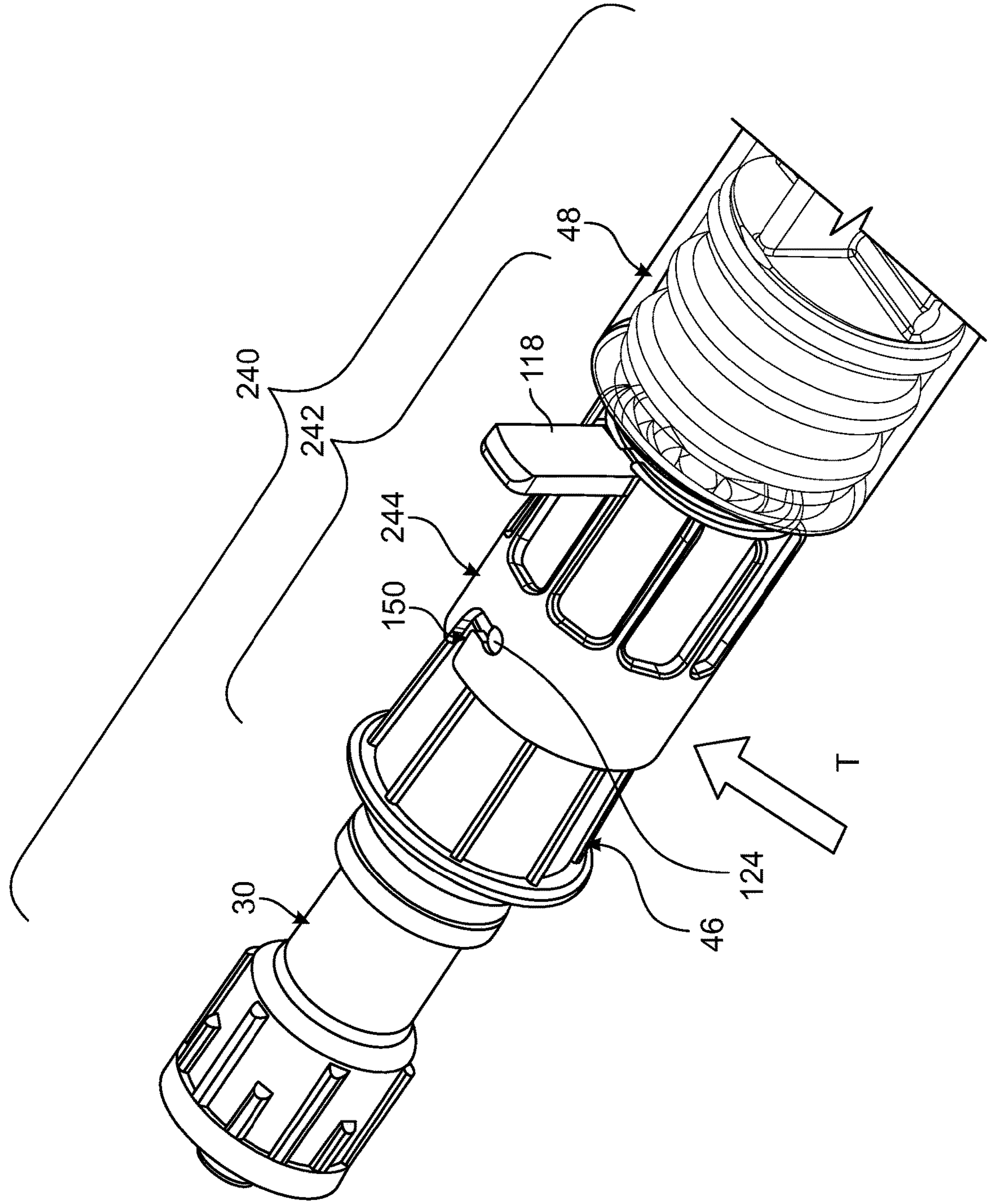
FIG. 13 is an isometric view of a third embodiment of a disinfection and flushing device of the present disclosure after coupling of its disinfection cap portion to an exemplary IV connector of a medical patient and after advancement of the flush syringe into engagement with the IV connector.
Figure 14:
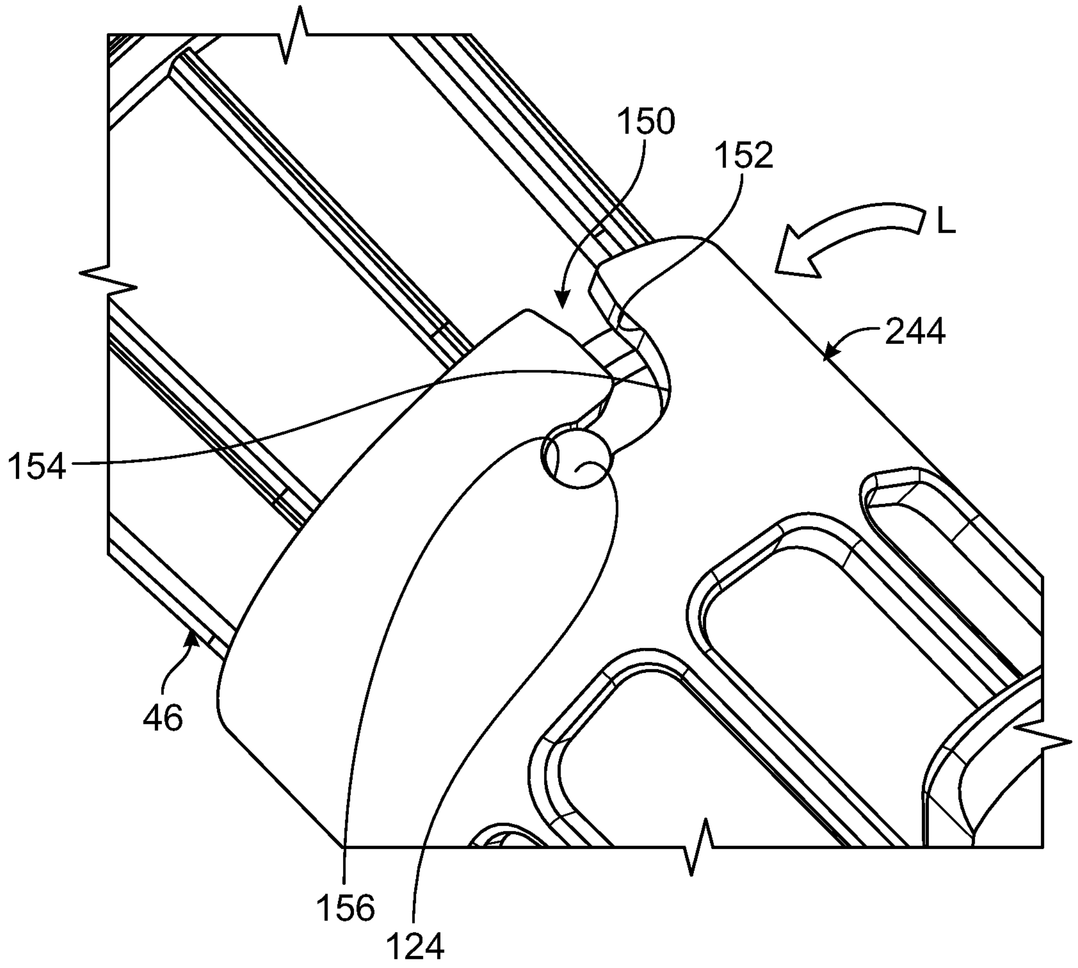
FIG. 14 is a detailed isometric view of a portion of the twist-lock, locking engagement mechanism of the embodiment of the device of FIG. 13.
Figure 15:
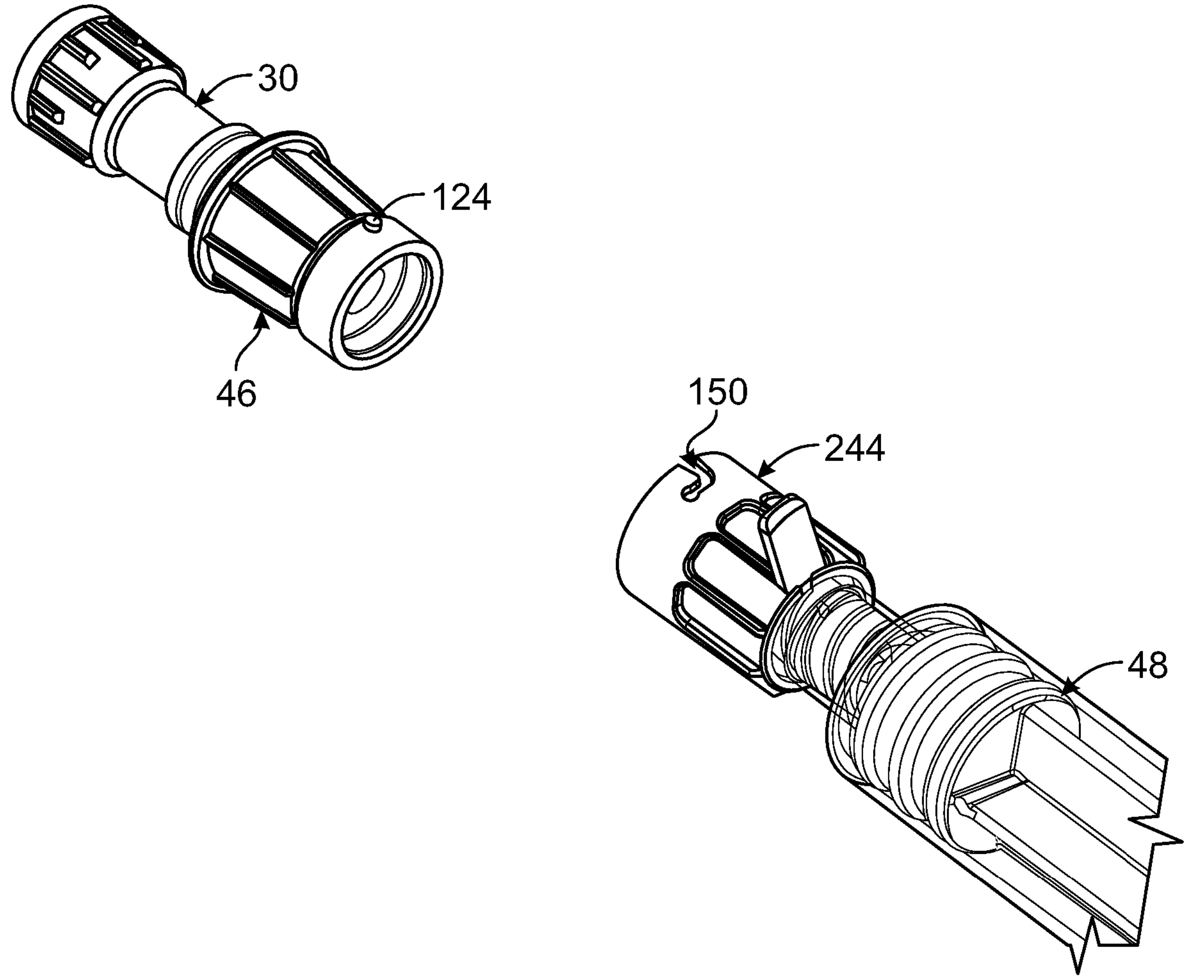
FIG. 15 is an isometric view of the device of FIGS. 13 and 14, after separation of the housing portion of the device and its attached flush syringe from the disinfection cap portion of the device, leaving the disinfection cap portion thereof coupled to the IV patient connector.
Figure 16:
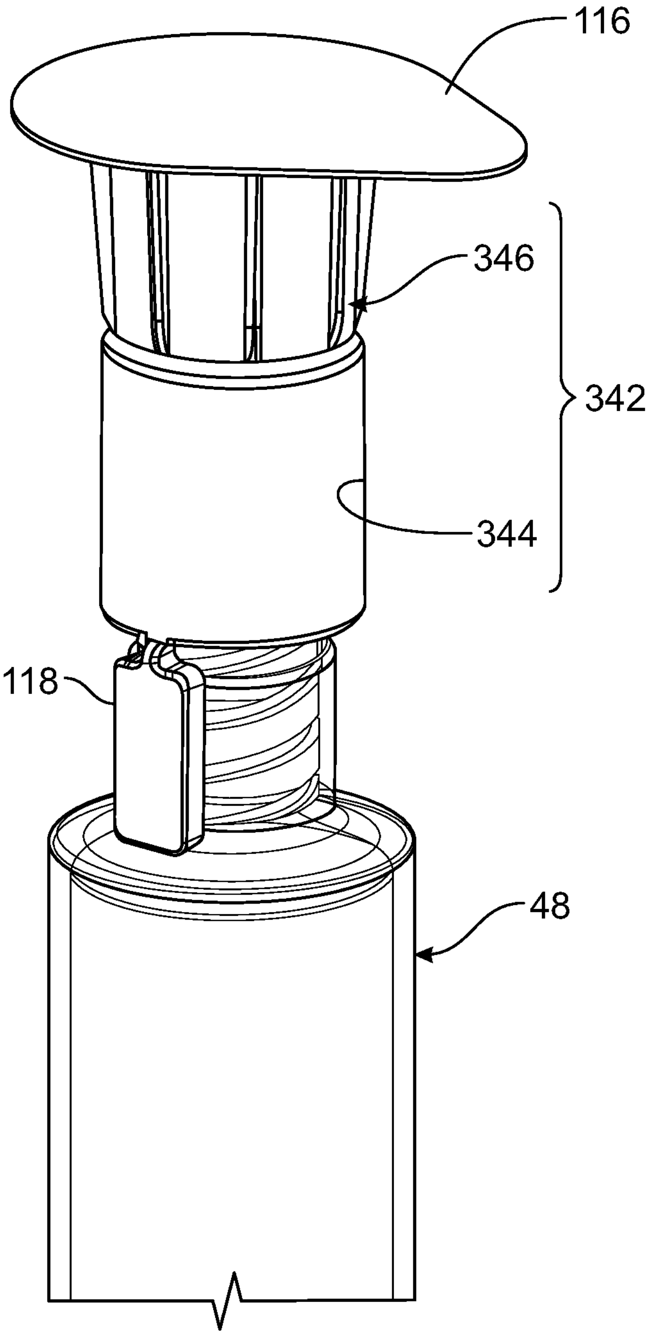
FIG. 16 is an isometric view of a fourth embodiment of a disinfection and flushing device of the present disclosure and an attached flush syringe.
Figure 17:
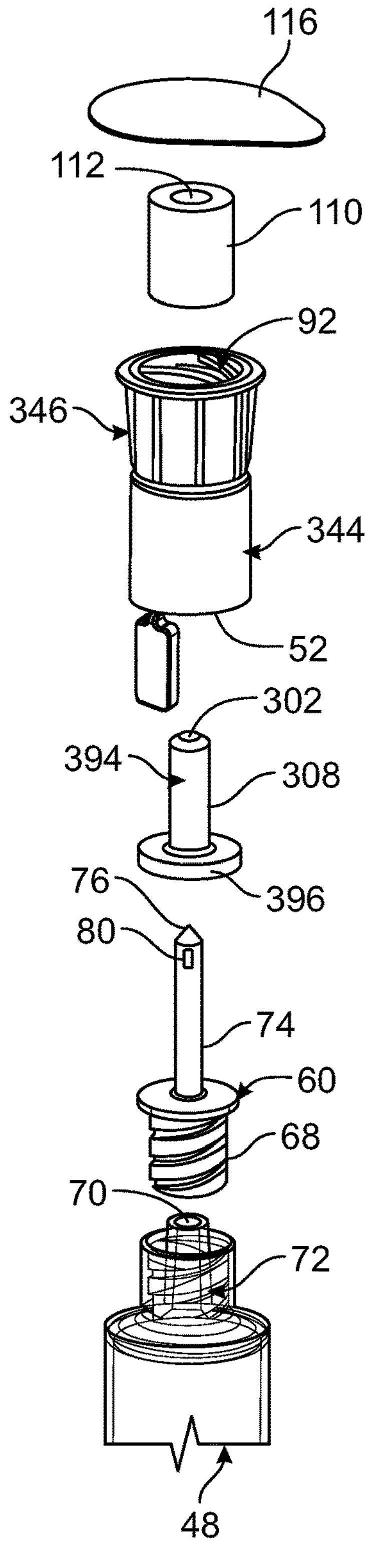
FIG. 17 is an exploded view of the device of FIG. 16.

FIGS. 13-15 depict a disinfection and flushing device 242 with a third, twist-lock, bayonet-type, locking-mechanism embodiment that always retains the disinfection cap 46 on the patient connector 30 after separation of the guide housing 244 and the spent syringe 48. The remainder of the structural components of the system and their operation correspond to those of the system 40 of FIGS. 1-8. The third embodiment of twist-lock mechanism comprises a bayonet pin 124 on the disinfection cap 46 and a J-shaped receptor slot 150 formed in the guide housing 244. The J-shaped receptor slot 150 comprises an axially aligned, fifth slot segment 152 and a curved, sixth slot segment 154. The lateral end of the sixth slot segment 154 terminates in a fifth necked serif 156 that retains the corresponding bayonet pin 124. The bayonet pin 124 is engaged within the fifth serif 156 when the second Luer connector 90 of the disinfection cap 46 portion of the entire assembled disinfection and flushing system 240 is engaged in threaded fashion and tightened upon the corresponding, threaded Luer connector 32 of the patient connector 30 (sec arrow T of FIG. 13). Conversely, when the guide housing 244 is loosened relative to the disinfection cap 46 (see arrow L of FIG. 14) the bayonet pin 124 only rides along the curved, sixth slot segment 154 and aligns with the axially aligned, fifth slot segment 152. Relative retraction of the guide housing 244 then separates it from the disinfection cap 46, as shown in FIG. 15.

The disinfection and flushing device 342 of system 340, shown in FIGS. 16-20 is designed only for total separation from the patient connector 30 after completion of an IV flushing procedure. The device 342 is suitable for disinfection and flushing of the patient connector 30, followed by drug administration through the patient connector. After drug administration the healthcare provider optionally may utilize one of the previously described devices 42, 142, or 242 to disinfect and flush the patient connector 30 and thereafter leave the disinfection cap 46 in situ on the patient connector.

Figure 18:
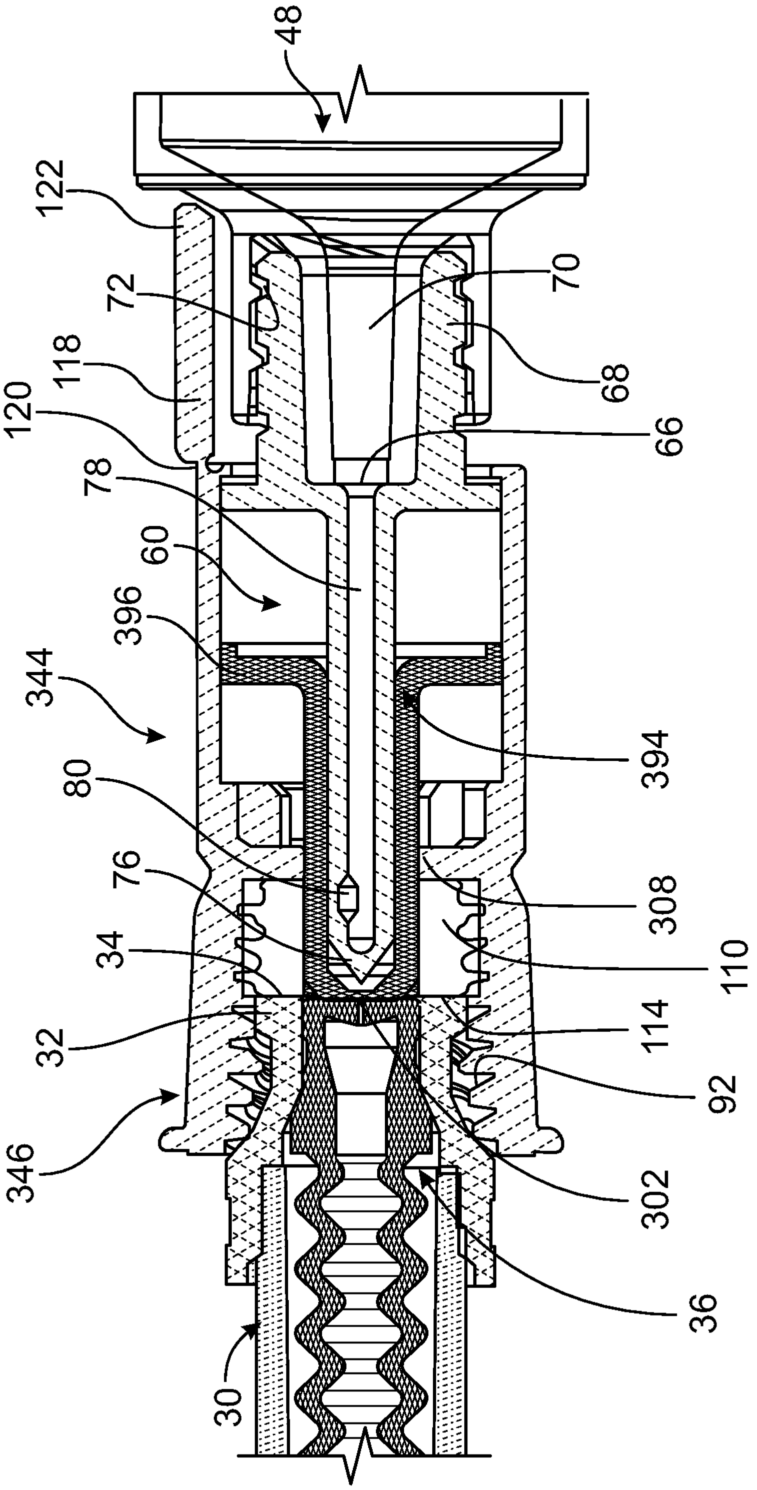
FIG. 18 is an axial cross-sectional view of the device of FIG. 16, after coupling the disinfection cap portion thereof to the exemplary IV connector, prior to advancement of the flush syringe into engagement with the IV connector.
Figure 19:
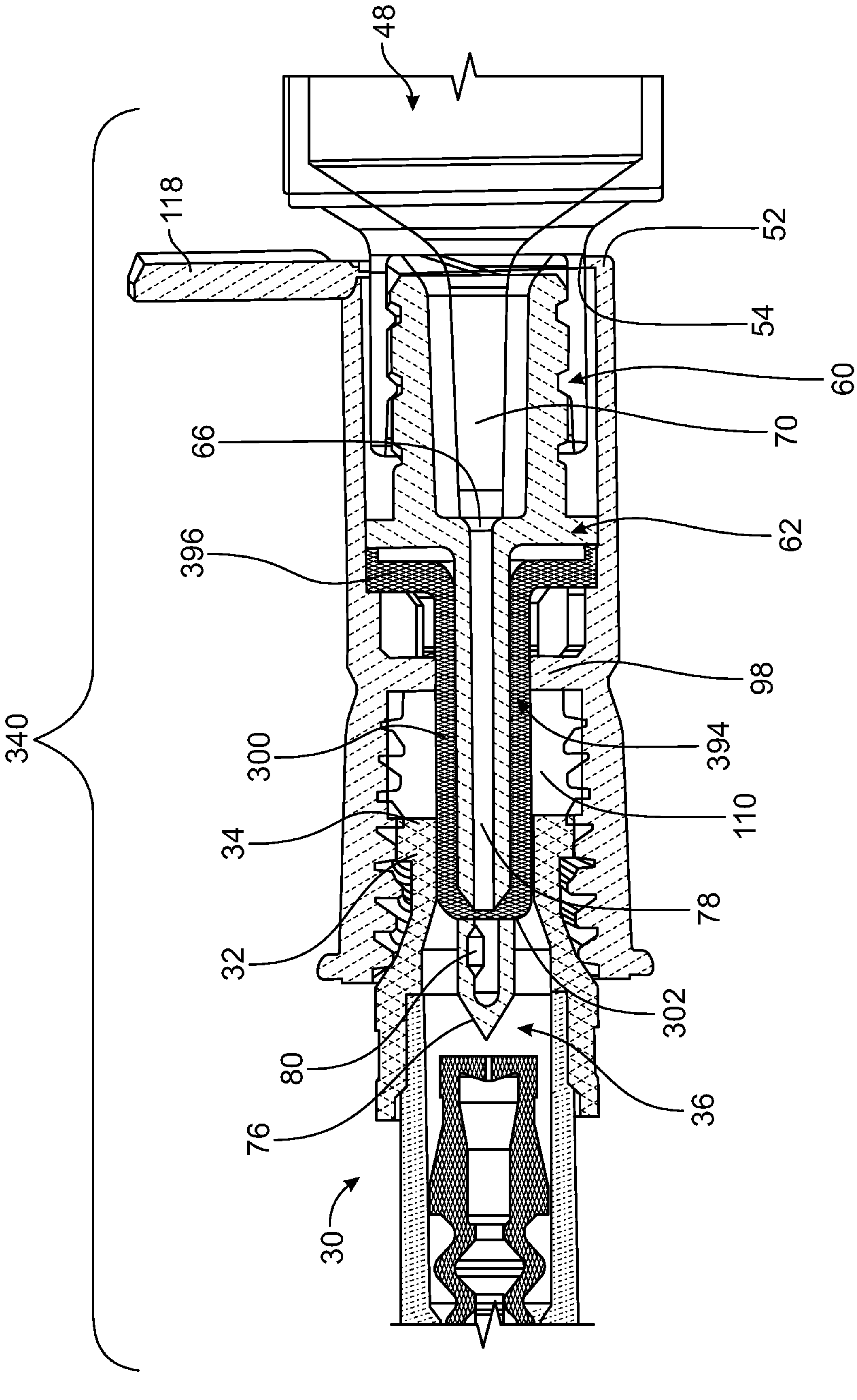
FIG. 19 is an axial cross-sectional view of the device of FIG. 16, after coupling the disinfection cap portion thereof to the exemplary IV connector, and after advancement of the flush syringe into engagement with the IV connector.
Figure 20:
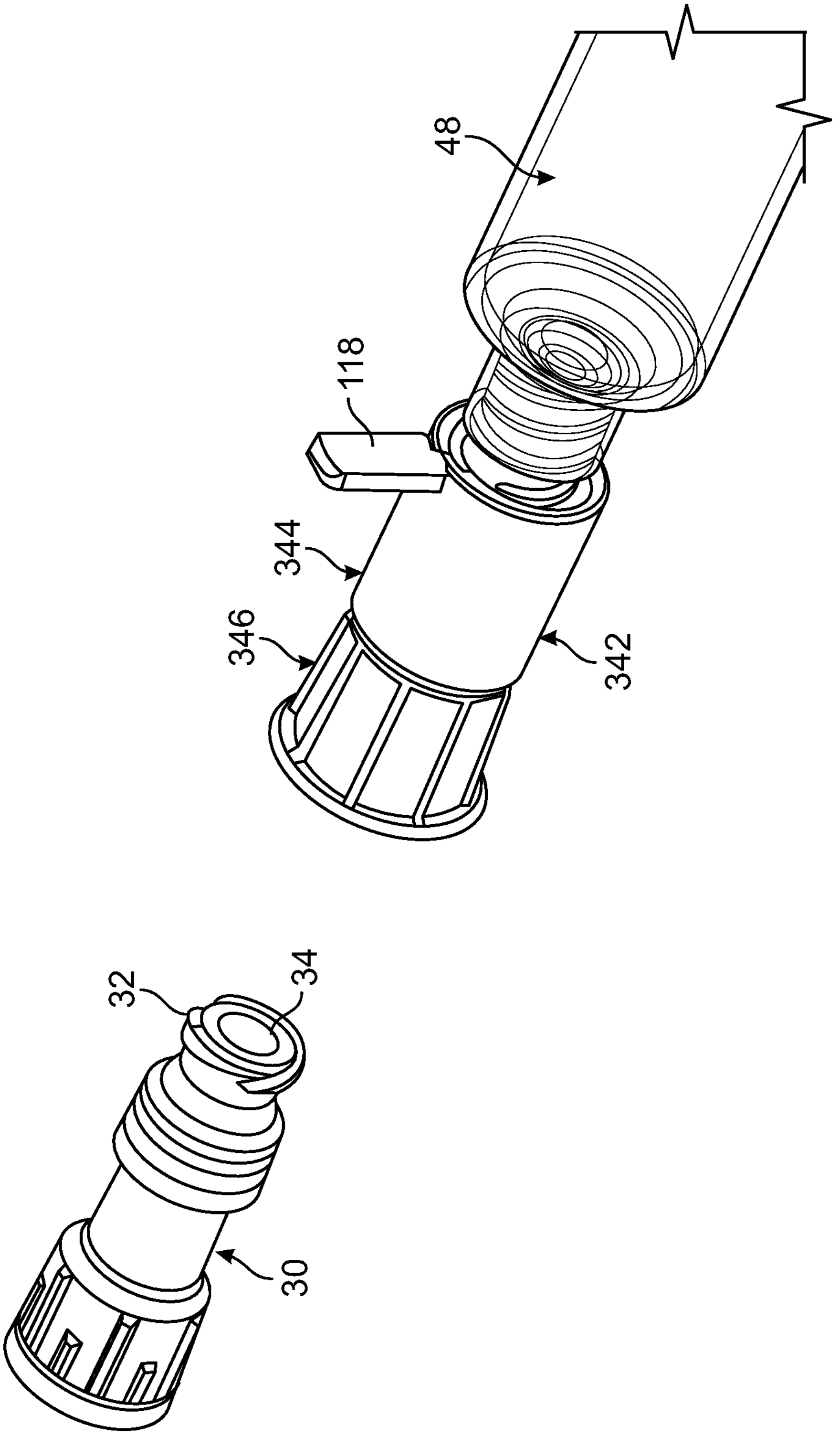
FIG. 20 is an isometric view of the device of FIG. 16 after its complete separation from the IV patient connector.

The device 342 permanently couples the guide housing 344 and the disinfection cap 346 to each other. After completion of a flushing procedure, the disinfection cap 346 is unscrewed from patient connector 30, as shown in FIG. 20. Internal components of device 342 generally function the same as those of the device embodiments 42, 142 and 242 of FIGS. 1-15. The components in device 342 that have substantially identical structure to corresponding components in the embodiments of FIGS. 1-15 share identical reference number designations in the drawings. For brevity, description of the structure and operation of the substantially identical components is not repeated. In FIGS. 16-20, those components with different structures comprise the unistructural guide housing 344/disinfection cap 346, and the elastomeric sleeve 394. Referring to FIGS. 18 and 19, the elastomeric sleeve 394 comprises a sleeve flange 396, a non-axially expanding, tubular shaft portion 300 and a distal tip 302 that is pierced by the spiked tip 76 of the end cap 62. In order to flush the patient connector 30, the guide housing lid 118 is pivoted to its second position to allow advancement of the end cap 62 and the coupled syringe 48 within the first internal cavity 60 and piercing of the distal tip 302 of the elastomeric sleeve 394 (see FIG. 19). Piercing of the distal tip 302 of the elastomeric sleeve 394 with the spiked tip 76 of the end cap 62 establishes a fluid communication path from syringe 48 through the outlet 80 of the end cap and in turn into the internal passageway 36 of the patient connector 30. As shown in FIG. 20, after completion of the patient connector 30 flushing process, the entire device 342 is unscrewed from the patient connector.

During assembly of device 342, the tubular shaft portion 300 of the elastomeric sleeve 394 is inserted through the internal bushing 98 formed within the guide housing 344/disinfection cap 346, followed by insertion of the end cap 62. Thereafter the annular-shaped, proximal end wall 52 is inserted within the first internal cavity 60, to retain and capture the end cap 62 within the internal cavity. The threaded Luer connector 72 of the syringe 48 is coupled to the corresponding first Luer connector 68 of the end cap 62 and the device 342 is ready for coupling to, disinfection and flushing of a patient connector 30, as shown in FIG. 18.

An exemplary process for using either of the device embodiments 42 or 142 of the present disclosure in performing a Saline-Administration of drug-Saline (SAS) or Saline-Administration of drug-Saline-Heparin (SASH) workflow process is as follows:

1. Remove the device 42 or 142 from its sterile packaging unit and affix a pre-filled flush syringe 48 (e.g., containing saline or heparin flush solution) to the end cap 62 in the guide housing 44, if not already affixed as a complete system device 40 in the packaging unit.
2. Remove the web peel lid 116 from the disinfection cap 46.
3. Connect the disinfection cap 46 to the patient connector 30; threaded connection of those components scrubs the patient connector with the disinfection pad 110; this assures sufficient disinfection of the connector (see FIG. 4).
4. Lift the guide housing lid 118 to its second position and advance the plunger 49 of the syringe 48 to advance the plunger and the end cap 62 within the guide housing 44 (see FIG. 5).
5. Initially pushing the plunger 49 advances the entire syringe 48 and the end cap's distal tip 76 to pierce the distal tip 102 of the elastomeric sleeve 94. Once distal tip 102 is pierced, the fluid path opens between prefilled syringe 48 and the patient connector 30 (see FIG. 5).
6. Continue to advance the plunger 49 to flush the patient connector 30 and its downstream VADs.
7. Upon completion of the patient connector 30 flush, there are two options:
   a. Hold the patient connector 30 stationary, while twisting the disinfection cap 46 counterclockwise, as shown by the arrow L in FIG. 11, to unscrew and separate the entire device 142 from the patient connector as part of an intermittent flushing procedure prior to administration of drugs to the patient through the patient connector and/or to continue with Saline-Administration-Saline or Saline-Administration-Saline-Heparin workflow (also possible with the devices 242 or 342); or b. Hold the disinfection cap 46 stationary, while twisting and pulling the guide housing 44 to disengage each of the respective locking mechanism's bayonet pin 124 from its corresponding female receptor slot 126, separating the guide housing and syringe 48 from the disinfection cap, leaving the cap coupled to the patient connector (also possible with the devices 142 or 242), as part of a SAS or SASH final flushing procedure.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A device for disinfecting and flushing of an intravenous patient connector, comprising:

a guide housing having an internal, first, circumferential wall surface, a proximal end wall defining a first through aperture therein, a distal end wall defining a second through aperture therein, and a first internal cavity defined within the first circumferential wall surface and the respective proximal and distal end walls;

an end cap captured within and translatable within the first internal cavity, a proximal end of the end cap defining an inlet and a first Luer connector adapted for engagement, through the first through aperture, with a corresponding Luer tip of a flush syringe, a distal end of the end cap defining a shaft with a spiked tip, the shaft defining an outlet and an internal lumen in fluid communication with the inlet and the outlet of the end cap;

a disinfection cap having an internal, second, circumferential wall surface, a proximal end wall defining a third through aperture for receipt of the shaft of defined by the distal end of the end cap, and a distal open end, the second circumferential wall surface defining a second Luer connector adapted for engagement with a corresponding Luer connector of a patient connector;

a second internal cavity defined within the circumferential wall surface of the disinfection cap which is structurally connected to the guide housing to facilitate the alignment of the first internal cavity and the second internal cavity;

the first internal cavity and the second internal cavity being aligned with each other so that the spiked tip of the end cap is translatable within the third through aperture into the second internal cavity;

an elastomeric sleeve captured within the second internal cavity, the sleeve having a proximal surface that is pierced by the spiked tip when the shaft defined by the distal end of the end cap is translated through the third through aperture, and a distal surface facing the open distal end of the disinfection cap; and a disinfection pad captured within the second internal cavity, intermediate the elastomeric sleeve and the distal open end of the disinfection cap, the pad defining a fourth aperture for exposure of the distal surface of the elastomeric sleeve to the distal open end of the disinfection cap, the disinfection pad defining a distal end surface adapted for disinfection of the patient connector when the disinfection cap is coupled to the patient connector;

wherein translation of the spiked tip of the end cap pierces the elastomeric sleeve and enables direct fluid communication between the inlet of the end cap and the distal open end of the disinfection cap.

2. The device of claim 1, further comprising a selectively engageable locking mechanism coupling the distal end wall of the guide housing to the proximal end wall of the disinfection cap.

3. The device of claim 2, further comprising the distal end wall of the guide housing and the proximal end wall of the disinfection cap nested and slidably engaged with each other, with selective engagement and separation thereof facilitated by engagement and disengagement of the locking mechanism.

4. The device of claim 3, wherein the selectively engageable locking mechanism comprising a twist connector.

5. The device of claim 4, wherein the twist connector comprising at least one bayonet pin formed on the guide housing or the disinfection cap and a corresponding receptor slot formed on the other of the guide housing or the disinfection cap.

6. The device of claim 5, wherein the at least one receptor slot having a T-shaped profile or an L-shaped profile or a J-shaped profile comprises a bayonet pin on the disinfection cap and a J-shaped receptor slot formed in the guide housing.

7. The device of claim 1, wherein the guide housing and the disinfection cap permanently coupled to each other.

8. The device of claim 1, wherein the elastomeric sleeve having a peripheral flange abutting the proximal end wall of the disinfection cap and a hollow, tubular stem projecting into the second internal cavity for receiving the shaft of defined by the distal end of the end cap, with a distal tip of the tubular stem pierceable by the spiked tip.

9. The device of claim 8, further comprising the tubular stem having expandable bellows configured to be axially expandable upon insertion of the shaft of defined by the distal end of the end cap therein.

10. The device of claim 1, further comprising the guide housing having a lid with a distal end thereof coupled to the housing and a proximal end thereof projecting axially away from the proximal end of the housing in a first position and displaced away from said proximal end of the housing in a second position, whereby when the lid is in its first position, it blocks advancement of the end cap within the first internal cavity of the guide housing, but allows said advancement when the lid is in its second position, said advancement enabling the spiked tip of the end cap to pierce the elastomeric sleeve.

11. The device of claim 1, further comprising a web peel lid covering the distal open end of the disinfection cap.

12. The device of claim 1, wherein the disinfection pad further comprising an antimicrobial material.

13. The device of claim 12, wherein the disinfection pad is compressible upon affixation of the disinfection cap to a patient connector.

14. The device of claim 1, wherein the first and/or the second Luer connector comprising a threaded Luer connector.

15. A system for disinfecting and flushing an intravenous patient connector, comprising:

a guide housing having an internal, first, circumferential wall surface, a proximal end wall defining a first through aperture therein, a distal end wall defining a second through aperture therein, and a first internal cavity defined within the first circumferential wall surface and the respective proximal and distal end walls;

an end cap captured within and translatable within the first internal cavity, a proximal end of the end cap defining an inlet and a first Luer connector, a distal end of the end cap defining a shaft with a spiked tip, the shaft defining an outlet and an internal lumen in fluid communication with the inlet and the outlet of the end cap;

a disinfection cap having an internal, second, circumferential wall surface, a proximal end wall defining a third through aperture for receipt of the shaft of defined by the distal end of the end cap, and a distal open end, the second circumferential wall surface defining a second Luer connector;

a second internal cavity defined within the circumferential wall surface of the disinfection cap which is structurally connected to the guide housing to facilitate the alignment of the first internal cavity and the second internal cavity;

the respective first internal cavity and the second internal cavity being aligned with each so that the spiked tip of the end cap is translatable within the third through aperture into the second internal cavity;

an elastomeric sleeve captured within the second internal cavity, the sleeve having a proximal surface that is pierced by the spiked tip when the shaft defined by the distal end of the end cap is translated through the third through aperture, and a distal surface facing the distal open end of the disinfection cap; and a disinfection pad captured within the second internal cavity, intermediate the elastomeric sleeve and the distal open end of the disinfection cap, the pad defining a fourth aperture for exposure of the distal surface of the elastomeric sleeve to the distal open end of the disinfection cap, the disinfection pad defining a distal end surface;

a pre-filled flush syringe having a syringe barrel containing a flushing solution, a translatable plunger within the syringe barrel, and a third Luer connector that is inserted through the first through aperture of the guide housing and coupled to the first Luer connector of the end cap, the inlet of the end cap in fluid communication with the flushing solution contained within the syringe barrel; and a patient connector including a connector body defining a fourth Luer connector coupled to the second Luer connector within the disinfection cap, with the distal end surface of the disinfection pad in contact with the fourth Luer connector;

wherein advancement of the flush syringe into the first cavity translates the spiked tip of the end cap, piercing the elastomeric sleeve and enabling fluid communication of the flushing solution between the pre-filled flush syringe and the patient connector, via the inlet, internal lumen and outlet of the end cap, and wherein advancement of the translatable plunger dispenses the flushing solution into the patient connector.

16. The system of claim 15, further comprising a selectively engageable locking mechanism coupling the distal end wall of the guide housing to the proximal end wall of the disinfection cap, for selective separation of the guide housing and the pre-filled flush syringe from the disinfection cap.

17. The system of claim 16, wherein the selectively engageable locking mechanism comprising a twist connector.

18. The system of claim 17, wherein the twist connector comprising at least one bayonet pin formed on the guide housing or the disinfection cap and a corresponding receptor slot formed on the other of the guide housing or the disinfection cap.

19. The system of claim 18, wherein the at least one receptor slot having a T-shaped profile or an L-shaped profile for facilitating selective separation of the guide housing and the flush syringe from the disinfection cap when the guide housing is twisted in a first direction relative to the disinfection cap and for removing the disinfection cap, along with the guide housing and the flush syringe from the patient connector when the guide housing is twisted in a second direction relative to the disinfection cap.

20. The system of claim 18, wherein the at least one receptor slot having a J-shaped profile for selective separation of the guide housing and the flush syringe from the disinfection cap when the guide housing is twisted in a first direction relative to the disinfection cap, leaving the disinfection cap coupled to the patient connector.

21. The system of claim 15, wherein the guide housing and the disinfection cap permanently coupled to each other, so that disconnection of the disinfection cap from the patient connector separates the entire system from the patient connector.

22. The system of claim 15, further comprising the guide housing having a lid with a distal end thereof coupled to the housing and a proximal end thereof projecting axially away from the proximal end of the housing in a first position and displaced away from said proximal end of the housing in a second position, whereby when the lid is in its first position, it blocks advancement of the syringe and the coupled end cap within the first internal cavity of the guide housing, but allows said advancement when the lid is in its second position, said advancement enabling the spiked tip of the end cap to pierce the elastomeric sleeve.

23. The system of claim 15, further comprising a web peel lid covering the distal open end of the disinfection cap.

24. The system of claim 15, wherein the disinfection pad further comprising an antimicrobial material.

25. The system of claim 24, the disinfection pad further comprising a compressible disinfection pad that compresses upon affixation of the disinfection cap to a patient connector.

26. The system of claim 15, wherein the corresponding pair of coupled first and third Luer connectors and/or the corresponding pair of coupled second and fourth Luer connectors comprising threaded Luer connectors.

* * * * *